(12) United States Patent
Jensen et al.

(10) Patent No.: US 9,457,347 B2
(45) Date of Patent: *Oct. 4, 2016

(54) OLEFIN METATHESIS CATALYSTS

(71) Applicant: Bergen Teknologioverforing AS, Bergen (NO)

(72) Inventors: Vidar R. Jensen, Bergen (NO); Giovanni Occhipinti, Kleppesto (NO); Frederik R. Hansen, Nesttun (NO)

(73) Assignee: Bergen Teknologioverforing AS, Bergen (NO)

( * ) Notice: Subject to any disclaimer, the term of this patent is extended or adjusted under 35 U.S.C. 154(b) by 0 days.

This patent is subject to a terminal disclaimer.

(21) Appl. No.: 14/269,007

(22) Filed: May 2, 2014

(65) Prior Publication Data
US 2014/0357478 A1    Dec. 4, 2014

Related U.S. Application Data

(62) Division of application No. 13/626,449, filed on Sep. 25, 2012, now Pat. No. 8,716,488.

(51) Int. Cl.
*C07F 15/00* (2006.01)
*B01J 31/22* (2006.01)
*B01J 31/24* (2006.01)
*C07C 6/04* (2006.01)

(52) U.S. Cl.
CPC .......... *B01J 31/2286* (2013.01); *B01J 31/226* (2013.01); *B01J 31/2265* (2013.01); *B01J 31/2278* (2013.01); *B01J 31/2404* (2013.01); *C07C 6/04* (2013.01); *C07F 15/00* (2013.01); *C07F 15/002* (2013.01); *C07F 15/0046* (2013.01); *B01J 2231/543* (2013.01); *B01J 2531/821* (2013.01)

(58) Field of Classification Search
CPC ................................. C07F 15/0046
See application file for complete search history.

(56) References Cited

U.S. PATENT DOCUMENTS 8,716,488 B2 * 5/2014 Jensen et al. ................. 548/103

* cited by examiner

*Primary Examiner* — Joseph Kosack
(74) *Attorney, Agent, or Firm* — Wolf, Greenfield & Sacks, P.C.

(57) ABSTRACT

The present invention refers to novel ruthenium- and osmium-based catalysts for olefin metathesis reactions, particularly to catalysts having stereoselective properties. Z-selectivity is obtained by utilizing two mono-anionic ligands of very different steric requirement. In olefin metathesis reactions these catalysts selectively provide the Z-isomer of disubstituted olefinic products.

10 Claims, 21 Drawing Sheets

Figure 1:
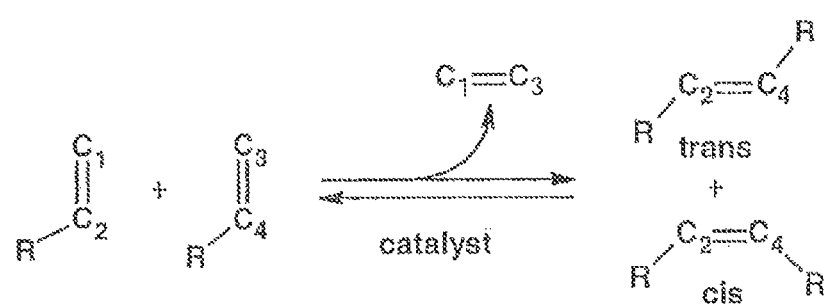

Stability: E1 > E2 and Z1 > Z2

OLEFIN METATHESIS CATALYSTS

CROSS REFERENCE TO RELATED APPLICATIONS

This application is a divisional application of U.S. patent application Ser. No. 13/626,449, filed Sep. 25, 2012, which claims benefit under 35 U.S.C. §365 of PCT International Application No. PCT/EP2011/065586, filed Sep. 8, 2011, which claims the benefit of European Patent Application No. 10175856.3, filed Sep. 8, 2010, the entire contents of the aforementioned applications are hereby incorporated herein by reference.

The present invention refers to novel catalysts for olefin metathesis reactions, particularly to catalysts capable of predominantly giving the Z-isomers of olefinic products.

BACKGROUND OF THE INVENTION

Catalysed olefin metathesis is one of the most flexible ways in which to make carbon-carbon bonds in general and double bonds (C═C) in particular (1, 2, 3). This reaction formally cleaves two different carbon-carbon double bonds (C═C) into four fragments that are recombined with two new C═C double bonds to form olefinic products in which the original fragment partners are exchanged. The last 5-10 years have seen an almost explosive increase in the use of this reaction for the production of fine chemicals, polymers and pharmaceuticals. The reaction is catalysed and the market for metathesis catalysts is reportedly worth $1.5 bn (12.5% of the total worldwide market for catalysts) and is expanding by 9-10% annually. Despite this success, an important problem remains: The product of this transformation is in general a mixture of cis (Z) and trans (E) disubstituted isomers, with the thermodynamically more stable E-isomer usually being the major component, see FIG. 1.

The biological, chemical and physical properties within a given pair of E- and Z-isomers may, in fact, be very different, highlighting the need for selective production of single isomers. The isomer mixtures produced have to be subjected to costly separation processes. Sometimes, the separation even turns out to be impossible (4).

The catalyst is the main key to controlling the ratio with which the isomers are formed and the availability of robust and industrially compatible stereoselective catalysts is expected to expand the applicability of olefin metathesis in organic synthesis and polymerisation chemistry (3). Such catalysts would have a particular impact on the synthesis of large macrocycles by ring closing metathesis (RCM). The Z-alkene functionality is, in fact, required in many cases, either because it is present in the target molecule or because it is necessary for subsequent stereospecific transformations. A range of natural products with biological activity (e.g. anticancer, antibacterial, and antifungal) contain Z-alkene macrocyclic frameworks, see Table 1. In most of the cases, the cost of extraction of these molecules is prohibitive, and total synthesis is the only alternative (4, 5). The formation of such large rings is very challenging, with RCM standing out among the few alternative routes (1, 5, 6). Unfortunately, the lack of stereocontrol in RCM (no existing catalyst affords stereoselective RCM) constitutes a serious drawback.

Due to the lack of stereocontrol in the olefin metathesis step, alkyne metathesis (i.e., triple-bond instead of double-bond metathesis) followed by Lindlar reduction is to date the most convenient synthetic route to manufacture most of compounds in Table 1 (4, 7, 8). However, due to the commercial importance of some target products, specific procedures have been elaborated to increase the yield of the Z-isomer and improve the isolation of the product (9).

TABLE 1

Representative examples of natural products to which synthetic access could be drastically simplified via cis-selective olefin metathesis.

| Natural product | Properties and application |
|---|---|
| Nakadomarine A | Anticancer, antifungal and antibacterial |
| Epothilone A ($) | Potent anticancer |
| Epothilone C ($) | Potent anticancer |
| Turrianes | Antineoplastic agents |
| Motuporamine C | Cytotoxic activity and/or anti-metaplastic activity. Robust inhibitor of chick neurite outgrowth |
| Cruentaren A | Highly cytotoxic F-ATPase inhibitor |
| Latrunculin A ($) | Actin-binding |
| Latrunculin B ($) | Highly selective actin-binding |
| Sophorolipid lactone | Microbial biosurfactant |
| Epilachnene ($) | Antiinsectan activity |
| Civetone ($) | Musk odor for perfumes |
| Yuzu lactone | Olfactory molecule |
| Ambretolide | Olfactory molecule |

($): commercial products

The stereochemical outcome is in general unpredictable and depends on many factors such as the nature of the substrate and of the catalyst, the reaction conditions and on the presence of specific additives (8-11). Time consuming and very costly empirical approaches are therefore required to improve the process of manufacturing the individual molecules. Hence, the quest for efficient stereoselective catalysts is to a large extent driven by commercial needs (3).

Recently, Schrock and Hoveyda have disclosed the first class of Z-stereoselective catalysts, (cf., for example, catalyst A, FIG. 2) (12-15). These new catalysts are based on molybdenum or tungsten and are capable of promoting metathesis transformations such as ring opening/cross metathesis (ROCM) (13), ring opening metathesis polymerisation (ROMP) (14), and cross-metathesis (CM) (15). However, to date, no examples of RCM have been reported. In addition, the catalysts based on molybdenum and tungsten are air and moisture sensitive and have limited functional groups tolerance. These problems are not specific to the new, stereoselective class, but are caused by the nature of the metal used and are shared by the entire family of Schrock catalysts (10). These are serious drawbacks for many industrial applications.

Several design strategies have been proposed for obtaining stereoselective ruthenium-based catalysts (catalysts B-D, cf. FIG. 2), but so far, both the selectivity and the generality resulting from these approaches have turned out disappointing (16).

U.S. Pat. Nos. 5,312,940, 5,342,909, 5,969,170, 6,111,121, 6,635,768 and 6,613,910, international patent applications WO 98/21214, WO 00/71554 and WO 2004/112951 disclose pentacoordinated ruthenium and osmium olefin metathesis catalysts. The content of those documents is herein incorporated by reference. These catalysts have the general structure:

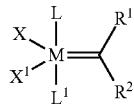

wherein M is the metal, L and L¹ are neutral ligands, R¹ and R² are H or organic moieties and X and X¹ are anionic ligands.

Similarly, hexacoordinated ruthenium and osmium olefin metathesis catalysts have also been disclosed, in U.S. Pat. No. 6,818,586 and US patent application US 2003/0069374. The content of those documents is herein incorporated by reference. These catalysts have the general structure:

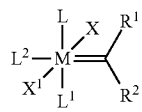

wherein M is the metal, L, L¹ and L² are neutral ligands, R¹ and R² are H or organic moieties and X and X¹ are anionic ligands.

In both the pentacoordinated and the hexacoordinated catalysts the two anionic ligands X and X¹ are preferably selected from halide and carboxylate anions. None of these catalysts, however, exhibit significant Z-stereoselectivity. U.S. Pat. No. 7,094,898 and US patent application US 2005/0131233 disclose ruthenium-based olefin metathesis catalysts with a high rate of catalytic turnover and a high degree of stability. The content of those documents is herein incorporated by reference.

The catalysts described in these documents have anionic ligands with the structure Z-Q, wherein each Z may comprise O, S, N or C and each Q comprises a planar electron-withdrawing group.

These documents also describe three novel asymmetrically substituted complexes Ru(OC₆Cl₅)Cl(CHPh)(IMes)(py), Ru(OC₆Br₅)Cl(CHPh)(IMes)(py) and (Ru(OC₆Br₅)Cl(CHPh)(IMes)(3-Br-py) that display a weak Z-stereoselectivity in the RCM of 5-hexen-1-yl 10-undecenoate to give oxa-cyclohexadec-11-en-3-one (Exaltolide). The product obtained using these catalysts contains 9-12% more of the Z-isomer than when using a symmetrically substituted catalyst. However, the Z-stereoselectivity of these asymmetrically substituted catalysts turns out not to be general. For example, in another RCM reaction reported in the same patent, the percentage of the Z-isomer product obtained using the asymmetrically substituted catalysts Ru(OC₆Cl₅)Cl(CHPh)(IMes)(py) and Ru(OC₆Br₅)Cl(CHPh)(IMes)(py)) is very similar to that obtained using two symmetrically substituted catalysts, RuCl₂(CHPh)(IMes)(py₂) and Ru(OC₆F₅)₂(CHPh)(IMes)(py).

These documents also report the only existing example of a ruthenium olefin metathesis catalyst with an anionic ligand in which a sulphur atom is bound to ruthenium (Ru(SC₆F₅)₂(CHPh)(IMes)(py)). However, only partial characterisation, consisting of ¹H-NMR and ¹⁹F NMR spectra, is provided for this compound. This catalyst displays good catalytic activity, surpassing that of the corresponding oxygen-based catalyst Ru(OC₆F₅)₂(CHPh)(IMes)(py), for example in the RCM of the 1,9-decadiene to give cyclooctene. However, no particular E/Z stereoselectivity is reported for this catalyst.

The present invention addresses the need for active and functional group tolerant stereoselective olefin metathesis catalysts by utilising anionic ligands of very different steric requirement. In olefin metathesis reactions, the thus obtained ruthenium and osmium catalysts selectively provide the thermodynamically less favoured Z-isomers. In addition to being Z-stereoselective, these catalysts display many of the attractive properties of commonly employed ruthenium-based catalysts for olefin metathesis. In particular, preferred embodiments of the invention are highly active catalysts and are fairly stable in air and moisture. Moreover, they have already shown tolerance towards esters and are also expected to be tolerant towards a number of other functional groups.

SUMMARY OF THE INVENTION

The present invention relates to a novel class of ruthenium and osmium olefin metathesis catalysts having a general formula (A) or (B) and isomers thereof:

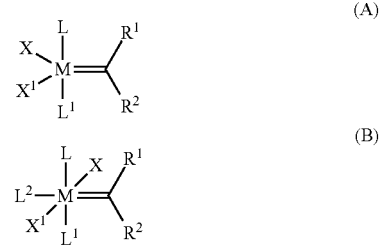

wherein
(i) M is ruthenium or osmium, preferably ruthenium,
(ii) L, L¹ and L² are independently selected from neutral electron donor ligands,
(ii) R¹ and R² are each independently H or an acyclic or cyclic organic moiety containing up to 30 C-atoms, and
(iv) X and X¹ are selected from anionic ligands,
wherein X and X¹ are different, and
wherein X is selected from halide or Z-Q,
wherein Z comprises O, N or C and each Q comprises a small and/or planar, preferably electron-withdrawing, group, and wherein X¹ is selected from Y—W, Y¹W(—W¹), or Y²—W(—W¹)(—W²), wherein Y comprises S, Se or Te, Y¹ comprises N, P, or As, preferably P or As, Y² comprises C or Si, preferably C, and wherein W, W¹, and W² are independently selected from C₁₋₂₀ acyclic, C₃₋₂₀ heterocyclic or cyclic, aliphatic or aromatic groups, preferably phenyl, that are unsubstituted or substituted with 1-20 electron-withdrawing groups, e.g. nitro, CF₃, halogen, CN, ester or keto groups, and/or one or more C₁₋₁₀ aliphatic or aromatic groups, and wherein W¹, preferably phenyl, and/or W² may also be independently selected from hydrogen,
or wherein any 2-3 of X, X¹, L, L¹, L², R¹, or R² are optionally covalently linked to form a chelating multidentate ligand.

A further aspect of the present invention is a catalyst for catalysing olefin metathesis reactions comprising a compound as described above. Preferably, the catalyst is capable of stereoselectively generating Z-isomeric products in olefin metathesis reactions.

The present inventors have found that stereoselectivity of olefin metathesis reactions may be provided by choosing a transition-metal complex having two different anionic ligands X and X¹, wherein X is selected from halide ions (e.g. I, Br, Cl or F ions) or small and/or planar ligands, whereas X¹ is selected from moderately large groups Y—W, Y¹—W(—W¹), or Y²—W(—W¹)(—W²), that possess the feature to form a relatively acute M-Y(Y¹,Y²)—W bond angle (in catalyst precursors of formula A and B (see above), the most acute of these angles could preferably be less than 120° and larger than 90°) with the metal M, such as thiolate, selenoate, or amide groups.

In the compounds of Formula (A) or (B), the groups L, $L^1$ and $L^2$ are neutral electron donors. The terms "neutral electron donor" and in particular "neutral electron donor ligand" are clear and common for the person skilled in the art. For example, the IUPAC Compendium of Chemical Terminology also known as the "Gold Book" uses the term "electron donor" (term ID=E01988) as well as the term "ligand" (term ID=L03518). L is preferably a neutral ligand selected from acyclic or cyclic carbene ligands, preferably N-heterocyclic carbene ligands, e.g. imidazol-2-ylidene ligands, or phosphines, e.g. aryl and/or alkyl phosphines, preferably trialkyl phosphines. Examples of N-heterocyclic carbene ligands are N,N'-bis(mesityl) imidazol-2-ylidene (IMes), N,N'-bis-(mesityl)-4,5-dihydroimidazol-2-ylidene (H$_2$IMes), N,N'-bis-[2,6-bis(1-methylethyl)phenyl]-4,5-dihydro-imidazol-2-ylidene, N,N'-bis($C_3$-$C_{12}$ aryl or $C_1$-$C_{12}$ alkyl) imidazol-2-ylidene, and N,N'-bis-($C_3$-$C_{12}$ aryl or $C_1$-$C_{12}$ alkyl)-4,5-dihydroimidazol-2-ylidene. Optionally, the C—C backbone of the imidazol-2-ylidene or of the imidazolidine ring can have one or more hydrogen atoms substituted by aryl or preferably by alkyl groups not linked together or covalently linked to form rings. Examples of trialkylphosphines are P(isopropyl)$_3$, P(cyclopentyl)$_3$ and P(cyclohexyl)$_3$.

$L^1$ and/or $L^2$ are any neutral ligands which may be independently selected from the group consisting of phosphines, sulfonated phosphines, phosphites, phosphinites, phosphonites, arsines, stibines, ethers, amines, amides, imines, sulfoxides, carboxyl compounds, nitrosyl compounds, thioethers, selenoethers. N-heterocyclic carbenes and unsubstituted or substituted aromatic N-heterocyclic compounds, e.g. pyridine.

In some embodiments, $X^1$ and $L^1$ and optionally $L^2$ are replaced by a chelating arylthiolate ligand substituted by one or more groups that may act as a neutral ligand, wherein said group may preferably be selected from halogen, e.g. chloro, bromo, iodo or fluoro, phosphine, sulfonated phosphine, phosphite, phosphinite, phosphonite, arsine, stibine, ether, amine, amide, imine, sulfoxide, carboxyl, nitrosyl, thioether, selenoether. The group which may act as a neutral ligand is preferably a substituent at the ortho-position of an aryl, e.g. phenyl ring, which forms the group W, $W^1$ or $W^2$, respectively.

In a specific preferred embodiment, $X^1$ is linked to $L^1$ forming a chelating hemilabile anionic ligand —$X^1$-$L^1$. This embodiment can thus be represented by the general formula (C) and isomers thereof:

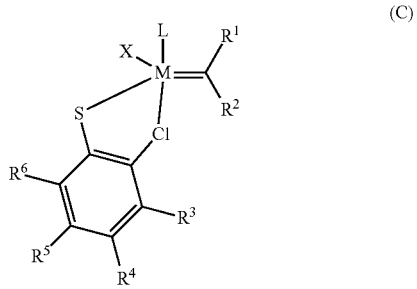

(C)

wherein $X^1$ and $L^1$ form a chelating arylthiolate ligand substituted in the ortho position with a chloride that acts as the hemilabile dative ligand, and wherein $R^3$, $R^4$, $R^5$, and $R^6$ are independently H, halogen, electron withdrawing groups, or $C_{1-20}$ acyclic, $C_{3-20}$ heterocyclic or cyclic, aliphatic or aromatic groups that are unsubstituted or substituted with 1-20 electron-withdrawing groups. The term "electron-withdrawing group" is well-known to the person skilled in the art. Again it is referred to the "Gold Book" already cited above using the terms "electron-acceptor" (term ID=E01976) as well as the term "group" (term ID=G02705). Examples of electron withdrawing groups are nitro, $CF_3$, halogen, CN, ester or keto groups.

In a preferred embodiment of the present invention, X is Z-Q. Z may be a group comprising O, N or C, e.g. O, —OC(O)—, or —NHC(O)—. More preferably, Z is O or —OC(O)—. Q preferably is a small and/or planar electron-withdrawing group. Z-Q may e.g. be selected from —OCO—$C_{1-2}$ (halo) alkyl, e.g. OCO—$CF_3$, OCO—$CF_2$H, OCO—$CFH_2$ or OCO—$CH_3$. Alternatively, Z-Q may be an alkyloxy, e.g. a $C_{1-2}$ (halo) alkyloxy group, such as —O—$CH_3$ or —O—$CF_3$, or an aryloxy group, e.g. a $C_{6-14}$ aryloxy group preferably substituted with at least one electron-withdrawing group, e.g. a nitro, $CF_3$, halogen, CN, ester or keto group. Substituents of aryloxy groups are preferably in the para-position (with regard to the O-atom of the aryloxy group). In an especially preferred embodiment, Z-Q is phenyloxy substituted in the para-position with an electron-withdrawing group as described above, such as para-nitrophenoxide.

The anionic ligand $X^1$ has the structure Y—W, $Y^1$—W(—$W^1$) or $Y^2$—W(—$W^1$)(—$W^2$) wherein Y comprises S, Se or Te, $Y^1$ comprises N, P, and As, and $Y^2$ comprises C and Si. Preferably, $X^1$ has the structure Y—W and Y is S or —SC(O)—, Se, —SeC(O)— or Te. More preferably, Y is S. W, $W^1$, and $W^2$ are independently selected from $C_{1-20}$ acyclic or $C_{3-20}$ cyclic or heterocyclic groups, aliphatic or aromatic groups. Accordingly, an especially preferred embodiment W is an aromatic group, in particular phenyl. $W^1$ and/or $W^2$ may also be independently selected from hydrogen. Acyclic groups are preferably selected from secondary or tertiary alkyl, e.g. $C_{3-10}$ alkyl groups. Heterocyclic or cyclic groups are preferably selected from heteroaromatic or aromatic, particularly phenyl groups. W, $W^1$, and $W^2$ may be substituted with 1-20, e.g. 1, 2, 3, 4, 5, 6, 7, 8, 9 or 10 electron-withdrawing groups, e.g. nitro, $CF_3$, halogen, CN, ester or keto groups and/or one or more $C_{1-10}$, preferably $C_{1-2}$ alkyl groups. Examples of such ligands are 2,3,4,5,6-pentafluorobenzenethiolate, 2,4,6-triphenylbenzenethiolate, 2,6-dichlorobenzenethiolate, 2-chloro-6-methylbenzenethiolate, 2-methylbenzene-thiolate, 2,6-dimethylbenzenethiolate, 2-trifluoromethylbenzenethiolate or 1,1,1,3,3,3-hexafluoro-2-(trifluoromethyl)-2-propanethiolate.

The groups $R^1$ and $R^2$ are independently selected from H or an acyclic or cyclic organic moiety preferably having up to 30 carbon atoms. For example, $R^1$ and $R^2$ are independently selected from the group consisting of H, $C_{1-20}$ alkyl, $C_{2-20}$ alkenyl, $C_{2-20}$ alkynyl, $C_{1-20}$ alkoxy, $C_{2-20}$ alkenyloxy, $C_{6-14}$ aryl, $C_{6-14}$ aryloxy, $C_{1-20}$ alkylcarboxylate, $C_{2-20}$ alkoxycarbonyl, $C_{1-20}$ alkylthio, $C_{1-20}$ alkylsufinyl or $C_{1-20}$ alkylsulfonyl, each optionally substituted with $C_{1-5}$ (halo) alkyl, halo, $C_{1-5}$ (halo) alkoxy, or phenyl optionally substituted with halo, $C_{1-5}$ (halo) alkyl or $C_{1-5}$ (halo) alkoxy.

A common, unifying characteristic of the individual embodiments of the present invention is that, in catalyst precursors of the general formula A and B (see above), the most acute angle formed by M, which is preferably Ru, and Y—W, Y—W¹ or Y—W², i.e., the bridgehead atom and the substituents of $X^1$, is in the range 90-120°.

Figure 18:
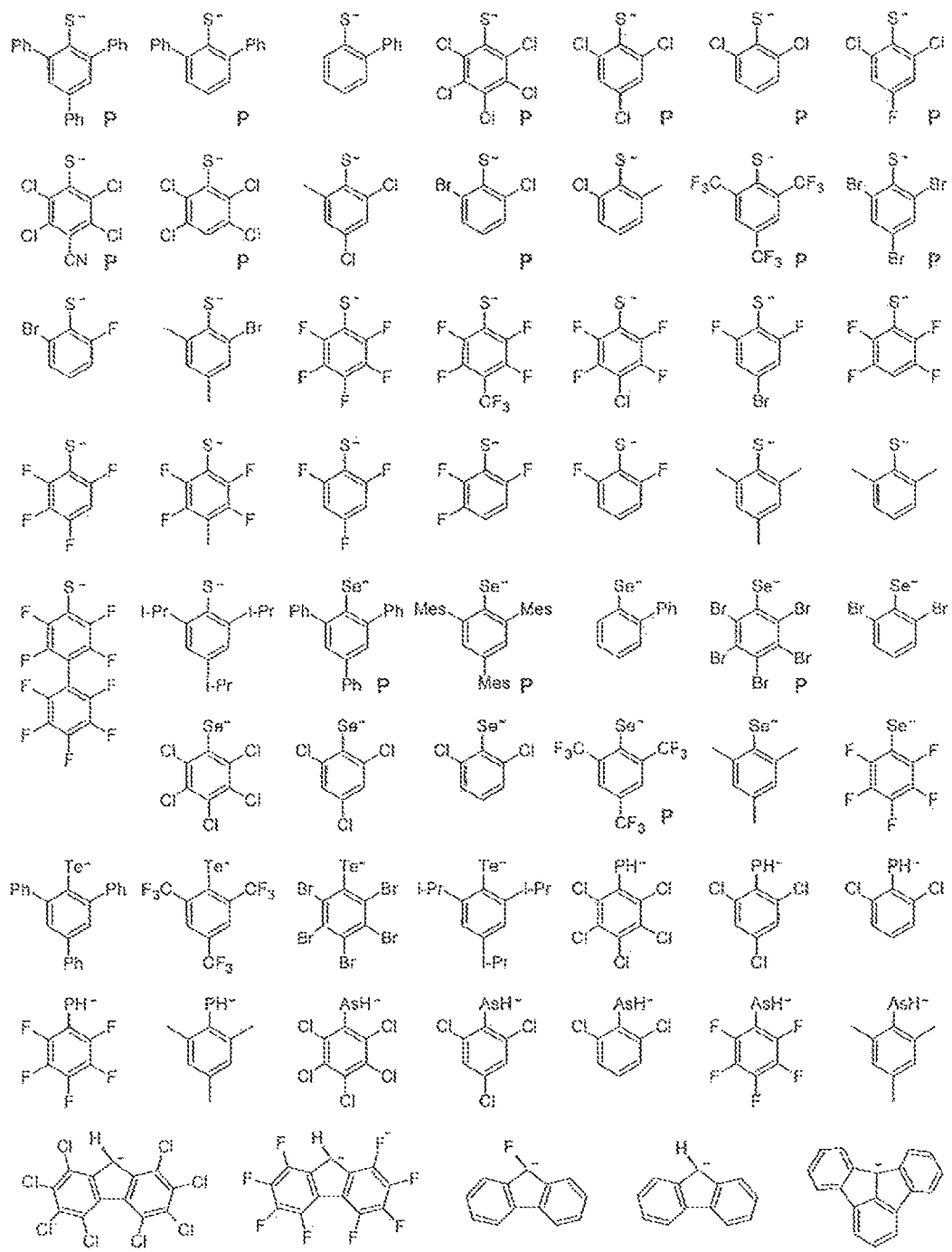

According to an especially preferred embodiment of the present invention, $X^1$ consists of Y—W, wherein Y is S, or Se and W is selected from the group consisting of 2,4,6-triphenyl-phenyl, 2,4,6-diphenylmethyl-phenyl, 2,4,6-tris (trifluoromethyl)-phenyl, 2,6-dimethyl-phenyl, 2,6-dichloro-phenyl or 2,3,4,5,6-pentachloro-phenyl. Further preferred embodiments of $X^1$ are shown in FIG. 18.

Figure 19:
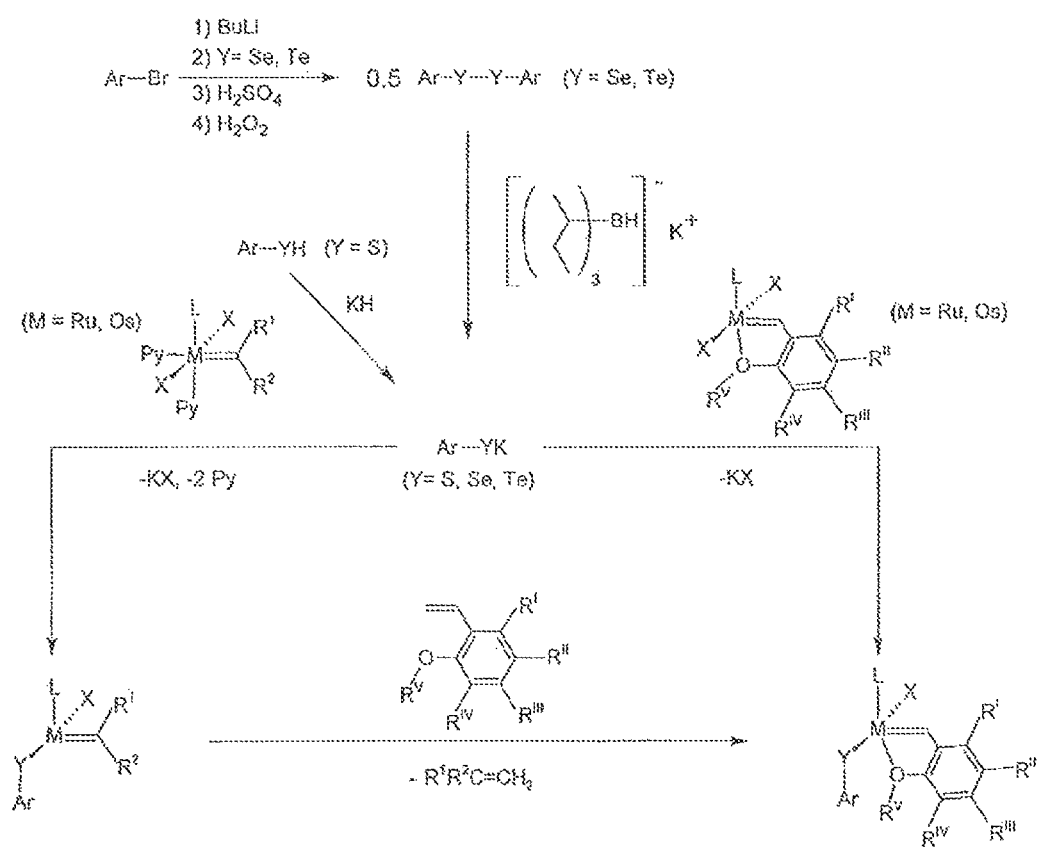
Figure 20:
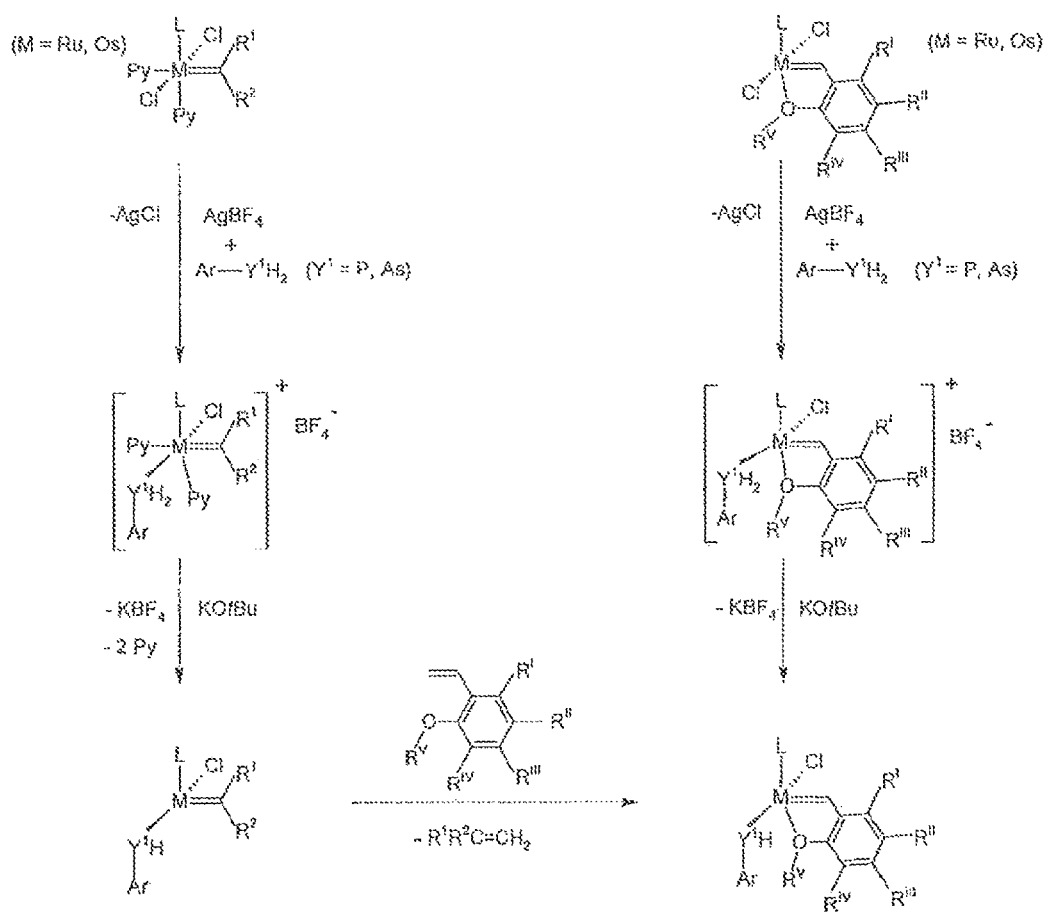
Figure 21:
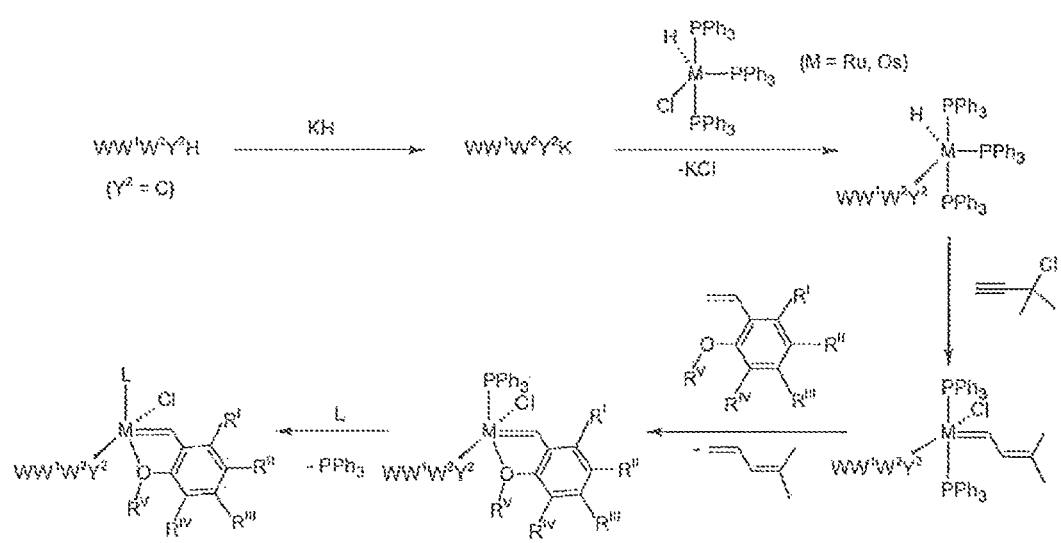

Synthetic approaches for the synthesis of catalysts based on different $X^1$ ligand types are shown in FIGS. 19-21.

The compounds of the present invention are suitable as catalysts, e.g. for catalysing olefin metathesis reactions. The olefin metathesis reaction may comprise a reaction selected from ring-closing metathesis, ring-opening metathesis, cross-metathesis, and ring opening metathesis polymerization. A preferred reaction is ring-closing metathesis.

Figure 6:
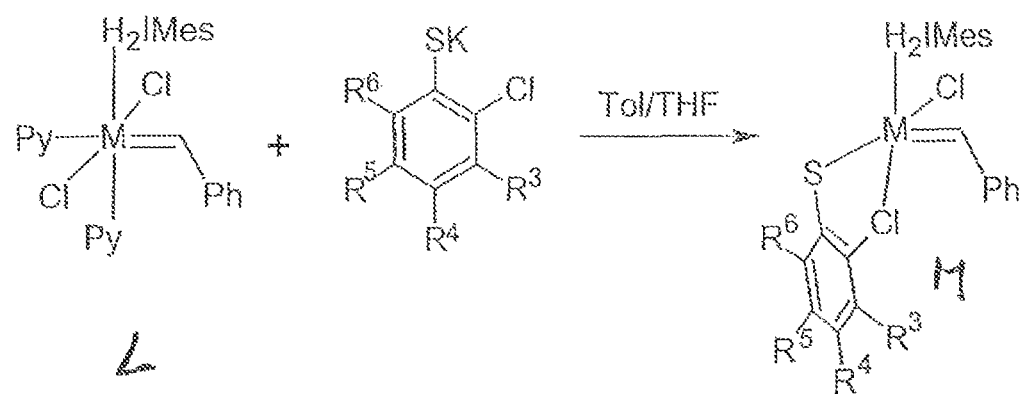

In preferred aspects, the catalysts are capable of stereoselectively generating Z-isomeric products. In especially preferred aspects, the catalysts are capable of stereoselectively generating Z-isomeric products in ring-closing metathesis reactions. In representative catalysed olefin metathesis reactions the Z/E selectivity using the novel catalysts is at least 10%, at least 20% or at least 30% (calculated on the total yield of Z and E products) higher than that obtained using a standard dichloro-substituted ruthenium catalyst otherwise similar to the inventive catalyst, for example see compound L in FIG. 6.

The catalyst of the present invention may be free in the reaction medium or bound to a solid support, e.g. inorganic supports such as glass beads, or magnetic beads, or organic supports such as sepharose or polystyrene.

The compounds of the invention are distinguished from prior art catalysts in that the two anionic ligands are not identical and have substantially different steric requirements. To achieve this difference in steric requirement the present inventors have found that one of the anionic ligands should form a relatively acute (the most acute of angles formed by this anionic ligand should preferably be less than 120° and larger than 90°) bond angle between the metal, the coordinating atom of the anionic ligand (Y, Y¹, Y²) and its substituent group (W, W¹, W²). In addition to this requirement on one of the anionic ligands, the second anionic ligand may preferably be of little steric requirement and be small and/or planar, and preferably electron withdrawing.

The compounds are conveniently prepared by reaction of a suitable ruthenium hydride with a propargyl chloride, as first demonstrated by Volland et al. for preparation of the dichloro substituted catalysts (17). Here, the reaction route of Volland et al. (17) has been modified in the following way: The chloride ligand of the ruthenium hydride employed is replaced with the anionic ligand of interest, e.g. a thiocarboxylate or a thiolate. Subsequently, the modified hydride complex, as prepared in situ, is reacted with a propargyl chloride to give the corresponding alkylidene complex.

This procedure has two main advantages: i) The option of selectively preparing compounds where only one halide has been replaced with any other anionic ligand, and ii) the ability to create compounds which are not easily prepared by direct reaction between the anionic ligand and the first or second generation Grubb's catalysts or other dihalide ruthenium alkylidene complexes.

A further advantage is the option of using potassium or sodium salts of the anionic ligand in question, thereby eliminating the need of toxic or environmentally harmful reactants such as thallium salts, which are typically employed when directly substituting chlorine with oxygen or sulphur ligands.

Figure 3:
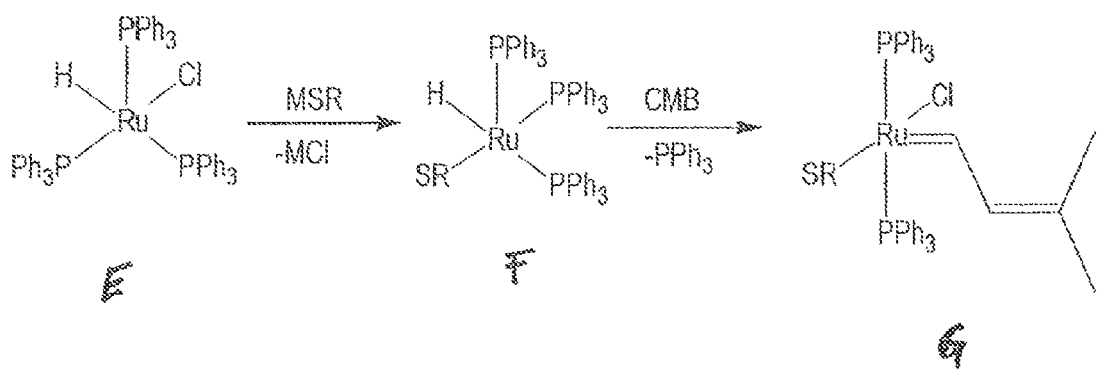

A reaction scheme for synthesising the thio-substituted compounds of the invention is shown in FIG. 3.

Some embodiments, for example those obeying the general formula (C) above, may also be prepared by reacting the potassium salt of the corresponding 2-chloro-arylthiolate ligand with a conventional dihalide ruthenium catalyst such as $(H_2IMes)(Cl)_2(Py)_2Ru$=CHPh.

Further, the present invention is explained in more detail by the following Figures and Examples:

FIGURE LEGENDS

FIG. 1: Metal-catalysed redistribution of C=C bonds.

FIG. 1 shows in particular a metathesis homocopling of propene to E- and Z-butene, as well as ethylene. The reaction provides a mixture of cis (Z) and trans (E) isomers.

Figure 2:
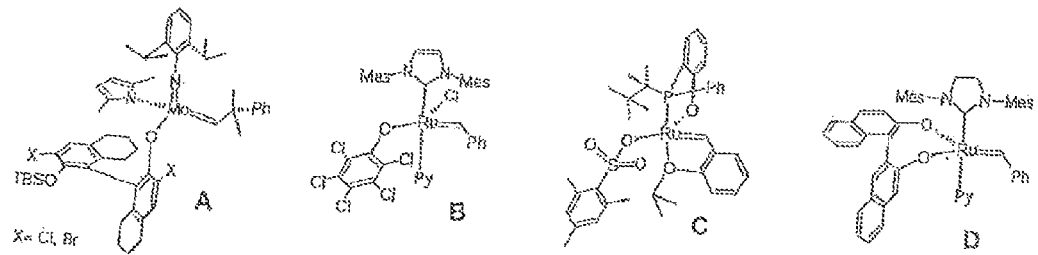

FIG. 2: Schrock-Hoveyda Z-stereoselective catalysts A and attempts at developing Z-stereoselective ruthenium-based catalysts B-D.

FIG. 3: A reaction scheme for preparation of thio-substituted ruthenium-based catalysts. CMB=3-chloro-3-methyl-1-butyne. The symbol "M" used in the formula MSR and MCl is K or Na.

Figure 4:

FIG. 4: Preparation of $(PPh_3)_3RuH(SCOPh)$.

Figure 5:
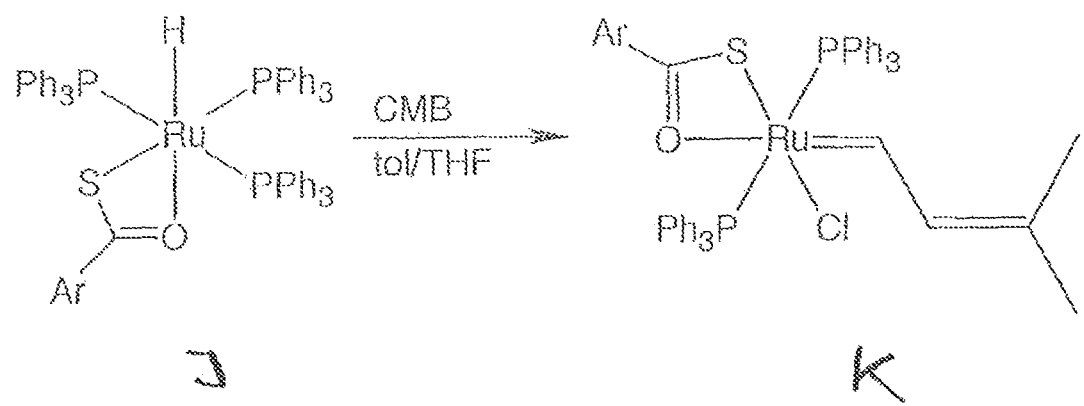

FIG. 5: Preparation of $(PPh_3)_2Cl(SCOPh)Ru$=CHCHC $(Me_2)$, CMB=3-chloro-3-methyl-1-butyne FIG. 6: Preparation of $(H_2IMes)Cl(S(2-Cl,3-R3,4-R4,5-R5,6-R6)Ph)Ru$=CHPh, compound M.

Figure 7:
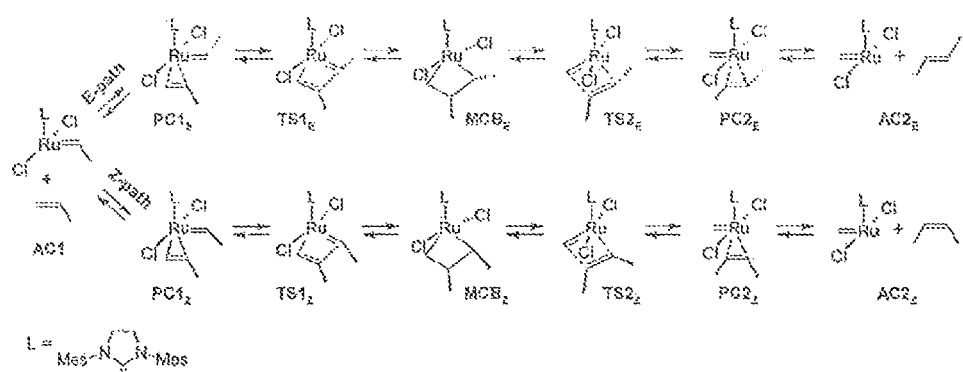

FIG. 7: Reaction pathway for the metathesis of $(H_2IMes)$ $Cl_2Ru$=CHMe complex with propene leading to corresponding E- (via the E-path) and Z-butene (via the Z-path) products.

Figure 8:
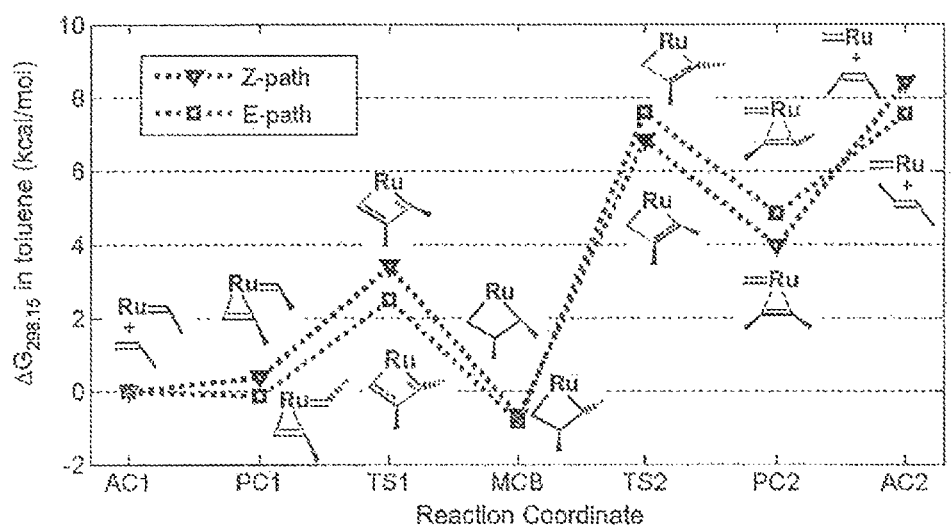

FIG. 8: Calculated Gibbs free energy profile (using the wB97XD) of the productive olefin metathesis reaction between $(H_2IMes)Cl_2Ru$=CHMe and propene in toluene.

Figure 9:
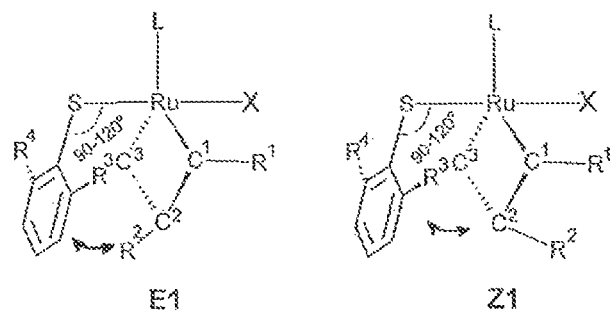

FIG. 9: Steric interaction between the thiophenolate ligand and the lowest part of the metallacyclobutane.

Figure 10:
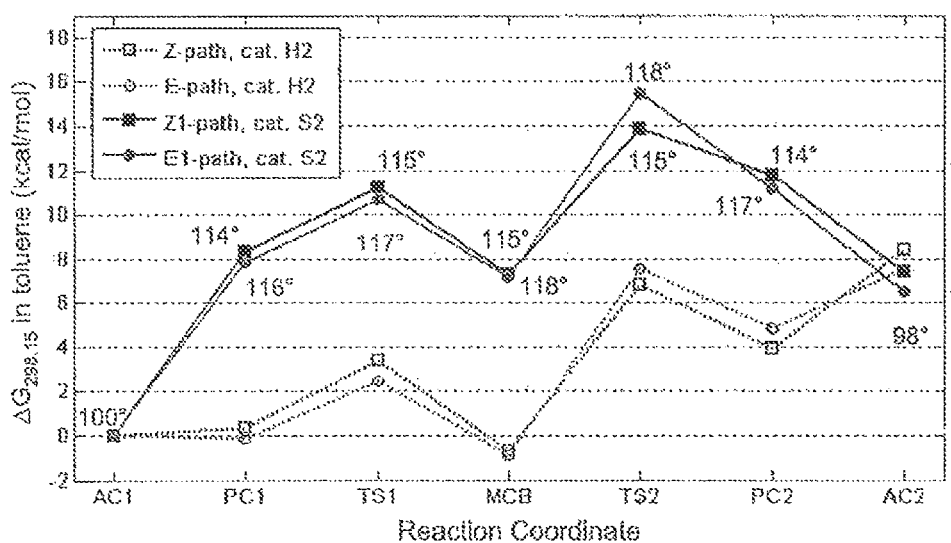

FIG. 10: Gibbs free energy (obtained using the wB97XD functional) profile in toluene solution for the homocoupling of propene promoted by S2 (solid lines) and H2 (dashed lines). The variation of angle)Ru—S—Ar(° during the reaction coordinate is given for each stationary point.

Figure 11:
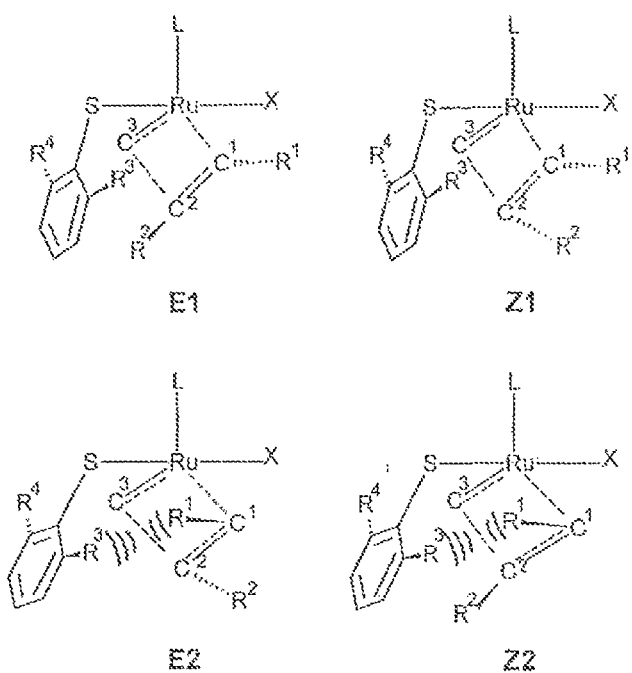

FIG. 11: Relative stability of the four stereoisomers of the saddle point TS2.

Figure 12:
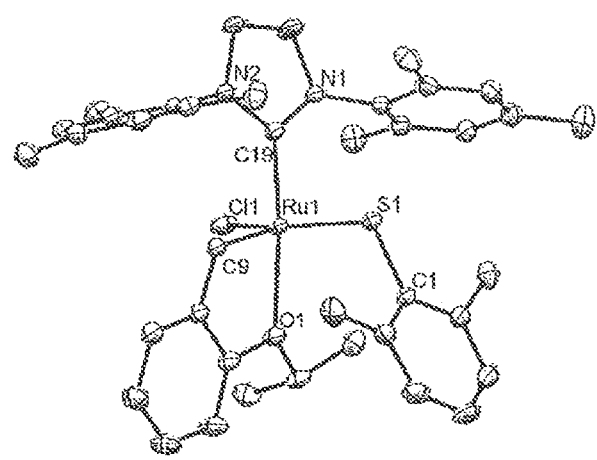

FIG. 12: ORTEP-style diagram of 4b with the thermal ellipsoids drawn at the 50% probability level. Hydrogen atoms have been omitted for clarity.

Figure 13:
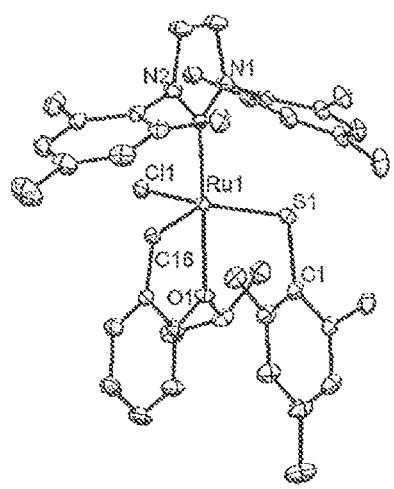

FIG. 13: ORTEP-style diagram of 4c with the thermal ellipsoids drawn at the 50% probability level. Hydrogen atoms and solvent molecule (fluorobenzene) have been omitted for clarity.

Figure 14:
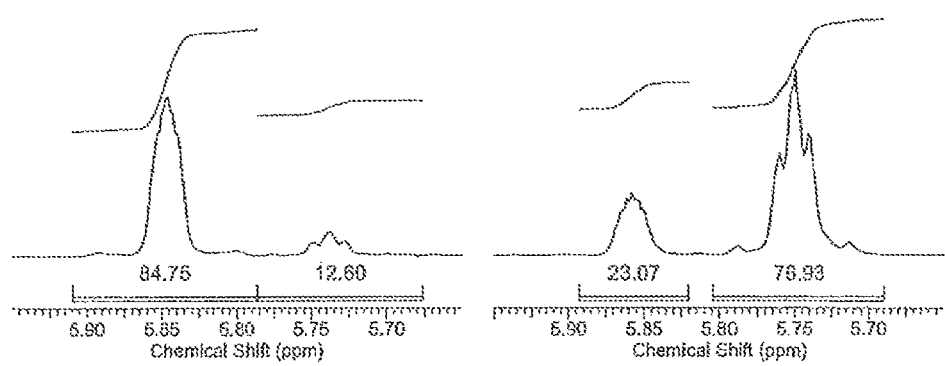

FIG. 14: ¹H NMR spectra of the vinylic protons (5.90-5.70 ppm) corresponding to E- and Z-1,4-diacetoxybut-2-ene as obtained using H2 (entry 1, left) and 4d (entry 5, right).

Figure 15:
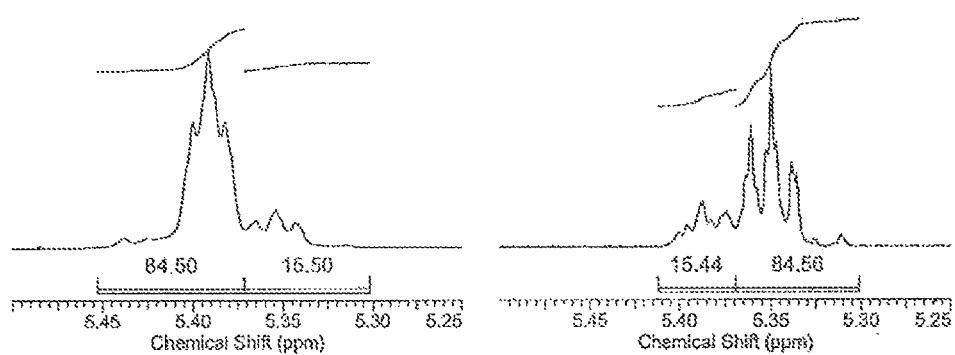

FIG. 15: ¹H NMR spectra of the vinylic protons (5.45-5.30 ppm) corresponding to (E)- and (Z)-5-decene as obtained using H2 (entry 1, left) and 4d (entry 10, right).

Figure 16:
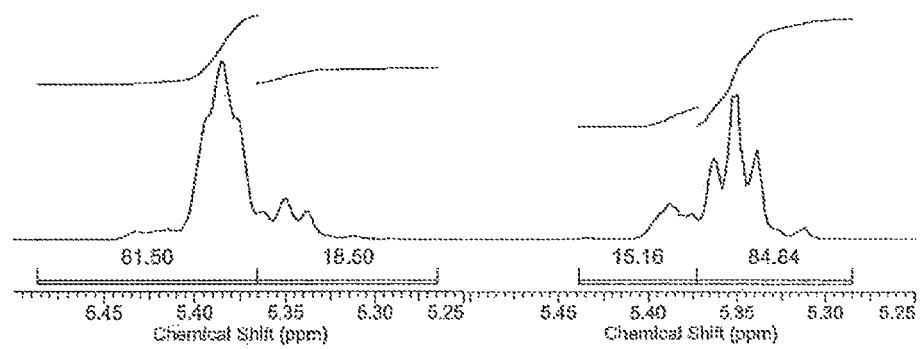

FIG. 16: ¹H NMR spectra of the vinylic protons (5.45-5.25 ppm) corresponding to (E)- and (Z)-7-tetradecene as obtained using H2 (entry 1, left) and 4d (entry 3, right).

Figure 17:
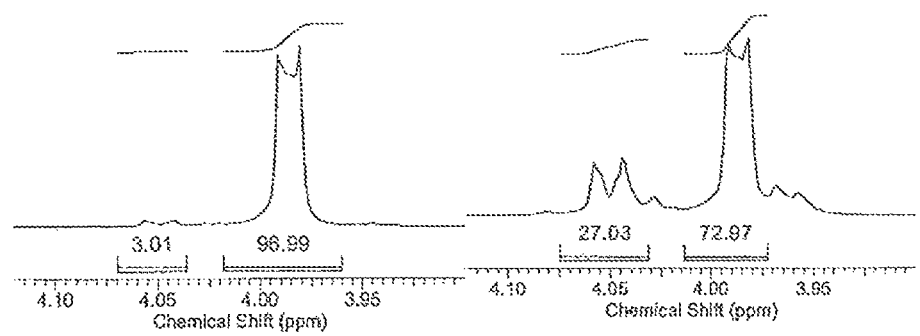

FIG. 17: $^1$H NMR spectra of the allylic protons corresponding to the Z-isomer (δ=4.05 ppm) and E-isomer (δ=3.98 ppm) as obtained using H2 (entry 2, left) and 3a (entry 3, right).

FIG. 18: Lewis structures showing examples of preferred ligands $X^1$. The most preferred ligands are indicated by a symbol P.

FIG. 19: Synthetic approaches to prepare catalysts adhering to the general formula A based on the ligand X1 being Y—Ar (Y=S, Se, Te, Ar=aryl) and with L1 and R2 covalently linked to form a chelating bidentate ligand.

FIG. 20: Synthetic approaches to prepare catalysts adhering to the general formula A based on the ligand X1 being Y1(-Ar)(—H) (Y1=P, As) and with L1 and R2 covalently linked to form a chelating bidentate ligand.

FIG. 21: Synthetic approaches to prepare catalysts adhering to the general formula A based on the ligand X1 being Y2(-W)(—W1)(W2)(Y2=C) and with L1 and R2 covalently linked to form a chelating bidentate ligand.

Compounds according to the present invention were characterised and/or provided by density functional theory calculations as well as by experimental reactions.

1. DENSITY FUNCTIONAL THEORY (DFT) CALCULATIONS

1.1 Introduction

The novel technology disclosed here has been developed using a tight integration of computational and experimental chemistry. The geometrical features of the ruthenium and osmium complexes necessary for obtaining Z-selective olefin metathesis complexes have been predicted by density functional theory (DFT) calculations and subsequently synthesized and tested in the laboratory. The correlation between the Z-selectivity predicted by the calculations and that observed in synthesized and tested examples is excellent, ensuring that also computational predictions so far not followed up by experiments can be trusted.

The basis for the design of the present Z-selective catalysts is a thorough understanding of the factors governing the stereoselectivity in ruthenium-based olefin metathesis catalysts, and this understanding has been obtained in via DFT calculations in which we have followed the olefin metathesis reactions leading to stereoisomers E and Z of the olefinic products. Based on these results, and also considering the commercial availability of the starting materials, we have designed a series of ruthenium and osmium metathesis catalysts that were predicted, by DFT calculations, to be Z-selective. We have selected and synthesized some of these predictions and measured the Z-selectivity in olefin metathesis transformations. Finally, we have constructed a linear model in which we have correlated the predicted and the experimental Z-selectivities. Next, by using this linear model we have estimated the experimental Z-selectivity in olefin metathesis for a range of novel ruthenium and osmium alkylidene complexes.

1.2 Factors Governing the Stereoselectivity in Ruthenium Metathesis Catalysts With the aim to gain insight into the factors that determine the stereoselectivity in ruthenium-based olefin metathesis catalysts, we have studied, by means of DFT calculations, the simplest olefin metathesis transformation which leads to a mixture of Z and E products, namely the homocoupling of propene, see FIG. 1.

We have investigated the steps of the catalytic process that determine the product stereoselectivity, i.e., those involved in the productive olefin metathesis reaction between the 14-electron Ru-ethylidene complex and propene (FIG. 7).

As catalyst for the initial mechanistic investigation we have chosen the 14-electron ethylidene complex (H$_2$IMes)Cl$_2$Ru=CHMe which is the active catalyst generated from a second generation metathesis precatalysts of the type (H$_2$IMes)LCl$_2$Ru=CRR" (e.g Grubbs- or Hoveyda-Grubbs second generation catalyst) after a predissociation step of the neutral ligand L and a cross-metathesis reaction with one molecule of propene. The latter reaction leads to exchange of the alkylidene ligand (Ru=CRR"→Ru=CHMe) and generates a molecule of CH$_2$=CRR". The precatalysts (H$_2$IMes)LCl$_2$Ru=CRR" are known to favor, in cross metathesis of terminal olefins, the formation of the thermodynamically more stable E-isomers (36).

FIG. 8 displays the Gibbs free energy profile in toluene of the reaction sketched in FIG. 7 obtained using the wB97XD (31) functional. A complete description of the methodology used is given in the Computational Details section.

These results, in agreement with those reported by Cavallo and coworkers (21), employing a slightly different DFT methodology, show that the transition state leading to rupture of the metallacyclobutane (TS2), and the product release (AC2) are the stationary points with the highest free energy along the reaction path and therefore are those that determine the stereochemistry of the products. In this case, albeit the break-up of the Z-metallacyclobutane is more facile than that of the E-isomer, the release of the Z-product is the energetically most costly step of the entire process. Thus, in agreement with our experimental results obtained for analogous homocoupling reactions, the formation of the thermodynamically more stable E-product is predicted to be predominant from the first catalytic cycle.

Since the E-product is the thermodynamically most stable, a Z-selective catalyst must be able to promote metathesis reactions that are under kinetic rather than thermodynamic control (i.e. $\Delta G^{\ddagger}_{TS2} > \Delta G_{AC2}$ or $\Delta G^{\ddagger}_{TS2} - \Delta G_{AC2} > 0$), and also have a lower barrier for formation of the Z-product, that is $\Delta G^{\ddagger}_{TS2(E)} > \Delta G^{\ddagger}_{TS2(Z)}$, see FIG. 8.

The first of these requirements ($\Delta G^{\ddagger}_{TS2} - \Delta G_{AC2} > 0$), also means that Z-selective catalysts will tend to be less active than catalysts that are not stereoselective such as the standard Grubbs second generation catalyst. Thus the magnitude of the difference, $\Delta G^{\ddagger}_{TS2} - \Delta G_{AC2}$ needs to be carefully tuned. A too small gap may be insufficient to guarantee the formation of the kinetic product, while a too large gap may result in insufficient catalytic activity. In contrast, the energy gap implied by the second requirement ($\Delta G^{\ddagger}_{TS2(E)} > \Delta G^{\ddagger}_{TS2(Z)}$), should ideally be as large as possible.

1.3 Design of Z-Selective Catalysts

In order to obtain the above-described modifications in the free energy profile of the metathesis reaction, to increase the Z/E ratio of the product, our strategy is to modify significantly the relative steric requirement of the two anionic ligands in such a way as to apply a stronger steric pressure on one side of the metallacyclobutane intermediate than the other, thus lowering the energy of the transition states for which the two substituents are on the same side (Z) relative to that of the transition states where the substituents are on the opposite side (E). In particular it is imperative to exert steric pressure in the region around the center (i.e., the $C^2$ atom in FIG. 9) of the three-carbon chain of the metallacyclobutane ring. At the same time, the corresponding steric pressure exerted by the other mono-anionic ligand should be low. Moreover, to maintain catalyst stability and activity, the steric pressure exerted in other parts of the catalyst (e.g. against the neutral ligand L and the alkylidene ligand and by these ligands themselves) should not be exaggerated.

In general we have found that the necessary steric pressure on one side of the catalyst can be obtained by ensuring that the most acute angle formed by the ruthenium atom, the bridgehead atom of the largest mono-anionic ligand (here termed $X^1$), and a substituent bonded to the latter atom (i.e., simply the Ru—Y—W angle when Y is two-coordinate such as is the case for S, Se or Te, or the most acute of the two angles R—Y—W and R—Y—$W^1$ when Y is three-coordinate such as is the case for P or As, or the most acute of the three angles R—Y—W, R—Y—$W^1$, and R—Y—$W^2$ when Y is four-coordinate such as is the case for C) is relatively sharp, preferably less than 120° when the complex is five or six coordinate (as, for example, the second transition state, TS2, or the relatively unstrained as in X-ray geometry of the corresponding precatalyst or less than 105° in case of the four-coordinate active complex, e.g. such as AC1 or AC2.

Thiophenolates bearing substituents in the ortho positions (see FIG. 9 and Chart 1 (S1-S9)) are examples of suitable and readily available ligands that give sufficiently sharp R—Y—W angles to exert the steric pressure necessary to obtain Z-selectivity. The substituents in the ortho-position of the thiophenolate ring take care of applying a sufficiently strong steric pressure in the highest region of the metallacyclobutane intermediate (i.e., close to $C^1$ and $C^3$ in FIG. 9), whereas the key feature that allows to direct efficiently the steric pressure towards the lowest part of the metallacyclobutane intermediate (i.e. around $C^2$ in FIG. 9) is the relatively sharp angle that the arylthiolate ligand forms with ruthenium (90°<Ru—S—Ar<120°). Bond angles in the same range can be obtained with various classes of anionic ligands having the following general structures: Y—W (Y=S, Se, Te), Y—W($W^1$) (Y=P, As), Y—W(—$W^1$)(—$W^2$) (Y=C), see Chart 1 and Table 3 for specific examples.

The rotation of the $X^1$ ligand around the Ru—$X^1$ bond alone or in combination with rotation around specific bonds of the $X^1$ ligand, e.g., the rotation of the aryl substituent around the S—Ar bond in the case of thiophenolates, might lead to alternative conformations of the ligand which are much less efficient in directing the steric pressure toward the substituents of the metallacyclobutane, in particular close to $C^2$. To minimize this risk and avoiding too large steric strains that may reduce the stability of the catalyst, the size and the shape of the dative ligand L should also be monitored. Therefore, we have analyzed the geometrical parameters of a large variety of DFT-optimized geometries of such Ru-based alkylidene complexes, and found out that most of the sterically demanding N-heterocyclic carbenes (e.g. 1,3-bis(2,4,6-trimethylphenyl)-4,5-dihydroimidazol-2-ylidene) ($H_2$IMes), (another name which is herein used interchangeably is N,N-bis(2,4,6-trimethylphenyl)-4,5-dihydroimidazol-2-ylidene)), 1,3-bis-[2,6-bis(1-methylethyl)phenyl]-4,5-dihydroimidazol-2-ylidene) and phosphines (e.g., tricyclohexylphosphine ($PCy_3$) commonly employed as the neutral ligand L in ruthenium metathesis catalysts are perfectly compatible with our suggested design for the large mono-anionic ligand $X^1$. Finally, to guarantee a reasonably high catalytic activity, the steric pressure applied by the second mono-anionic ligand on the other side of the metallacyclobutane intermediate must be relatively weak. Thus the second mono-anionic ligand should preferably be small (e.g. X=$Cl^-$, 4-nitrophenolate, $CF_3COO^-$).

Based on the above guidelines we have designed and investigated, using DFT calculations, the stereoselective properties of a series of ruthenium- and osmium-ethylidene complexes (Chart 1) in promoting the metathesis homocoupling of propene (FIG. 1) as a guide to the performance also in other olefin metathesis reactions. For comparison, a structurally closely related complex having a sterically demanding but "oxygen-coordinating" anionic ligand (O1) giving a Ru—Y—W angle>120° and a standard, non-stereoselective catalyst (H2), have also been included, see Chart 1.

In order to test the generality of our approach, for two representative catalysts (H2 and S2), the metathesis homocoupling of 1-hexene (i.e., pentylidene ligand and 1-hexene substrate) has also been studied.

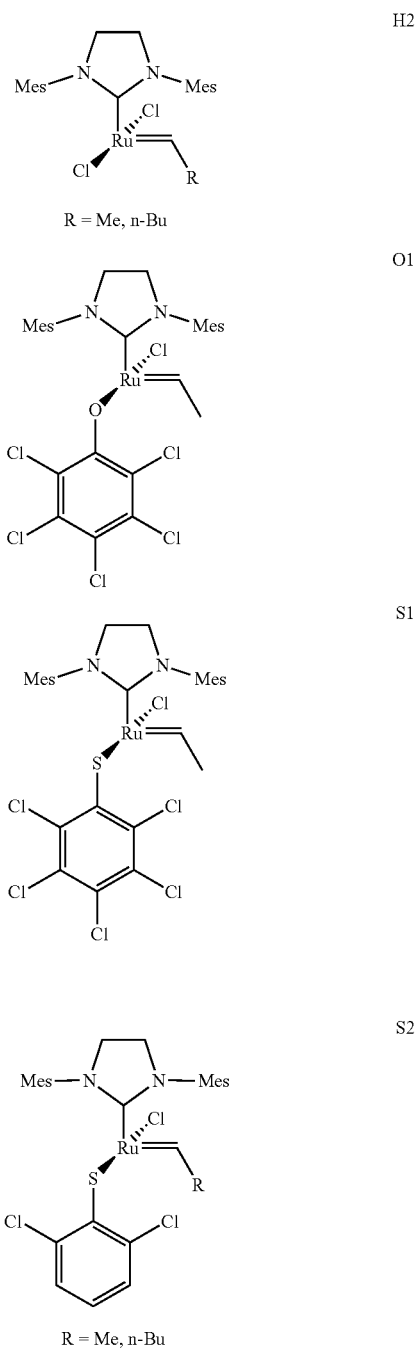

-continued
S3
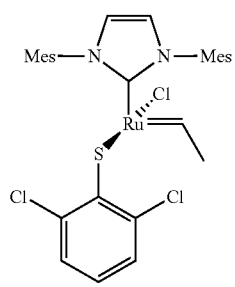
S4
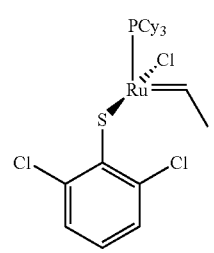
S5
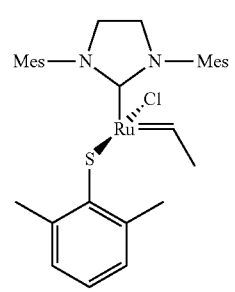
S6
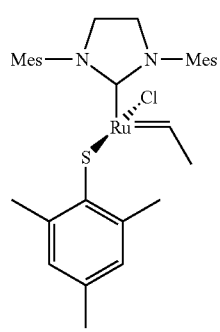
S7
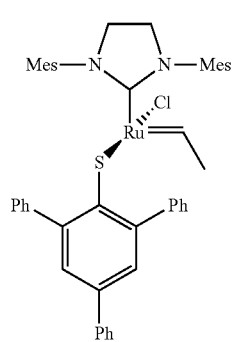
-continued
S8
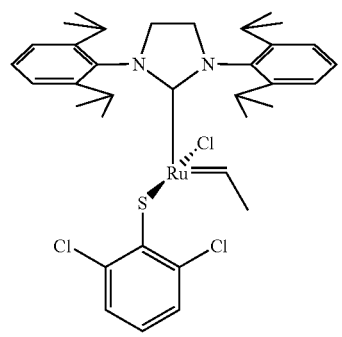
S9
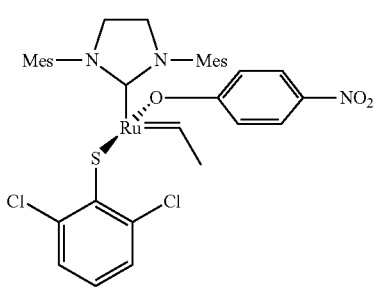
Se1
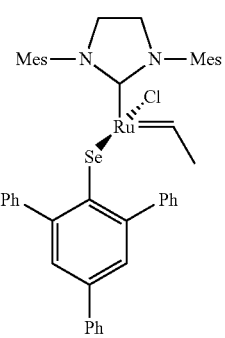
Te1
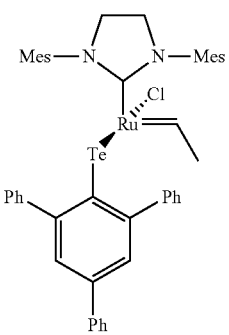
P1
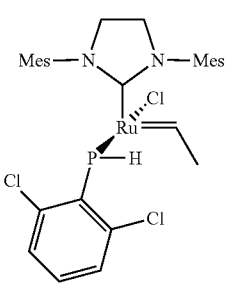

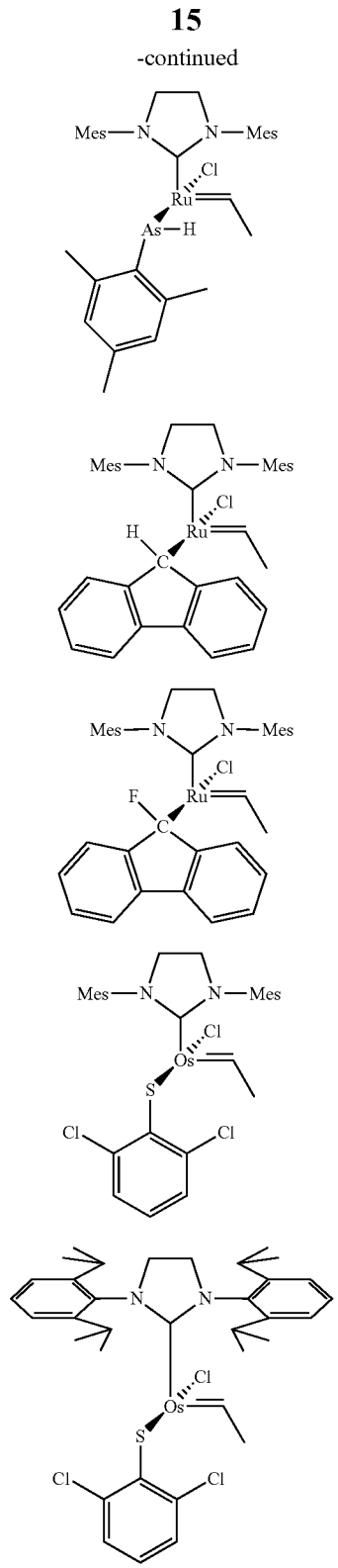

Chart 1. 14-electron ruthenium alkylidene complexes investigated by DFT calculations.

1.4 Z-Stereoselective Properties of the Complexes Shown in Chart 1

FIG. 10 compares the energy profiles calculated for the homocoupling of propene promoted by a classical, non-selective catalyst H2 (previously shown in Chart 1) and S2 respectively. Whereas the relative energies of the first (AC1) and the last (AC2) stationary points are comparable for H2 and S2, the energies involved in the formation/rupture of the metallacyclobutane intermediate (PC1, TS1, MCB, TS2, PC2) are systematically destabilized by 7-8 kcal/mol for S2.

In agreement with our expectation, the destabilization seen for the reaction of S2 appears to correlate well with the observed variation of the Ru—S—Ar bond angle (FIG. 10) and may be rationalized based on the fluctuation in this angle. If the general steric pressure in the complex is relatively low, as in the four-coordinate Ru ethylidene complex, a relatively acute Ru—S—Ar bond angle is observed (e.g., 100° calculated for the four-coordinate Ru ethylidene complex, AC1 for S2). The acute angle renders a region of the complex that later will be occupied by the metallacyclobutane intermediate (MCB) sterically encumbered. Thus in order to create sufficient space for the MCB, the Ru—S—Ar bond angle must become significantly more obtuse (by >14°) during the formation and breaking of the metallacyclobutane, and this increase in the bond angle, compared to its preferred value in the absence of steric pressure, costs additional activation energy for the olefin metathesis reaction to proceed.

As expected, more obtuse angles and correspondingly more pronounced destabilization (except for the 2-butene π-complex (PC2)) are observed in the E1-path and in particular for the kinetic barrier $TS2_{E1}$. Indeed, as depicted in FIG. 9 the E1-isomer of the metallacyclobutane needs some more space due to the methyl substituent of the carbon $C^2$ being directed towards the thiolate ligand ($X^1$) rather than towards the X ligand as for the Z-isomer.

Interestingly, the product release becomes slightly more facile, by 1 kcal/mol, compared to the standard catalyst H2, namely $\Delta G(AC2-AC1)_{S2} < \Delta G(AC2-AC1)_{H2}$. This small difference may be the consequence of a comparably less crowded structure for the methylidene (Ru—S—Ar=98°) than for the ethylidene-complex (Ru—S—Ar=100°).

For the catalyst S2 only the two most favorable reaction paths (the E1- and the Z1-path) have been considered, see FIG. 10 and FIG. 11 and Table 2. The other two paths (E2 and Z2) are energetically less favored because they require the formation of even more crowded minima and saddle points. In the latter geometries the methyl substituent at $C^1$ is pointing towards one of the ortho-substituents of the thiolate ligands, see FIG. 11. Thus, the formation of such alternative stereoisomers requires even more obtuse Ru—S—Ar angles, farther removed from their preferred values in the absence of steric pressure, and therefore also higher energies, see Table 2. A visual analysis of several optimized geometries strongly suggests that the same arguments are valid also for the other complexes shown in Chart 1.

TABLE 2

Relative stability of Z1-, Z2-, E1-, and E2-isomer of TS2.

| Catalyst | $\Delta G^{\ddagger}TS2_{Z1}$ | $\Delta G^{\ddagger}TS2_{Z2}$ | $\Delta G^{\ddagger}TS2_{E1}$ | $\Delta G^{\ddagger}TS2_{E2}$ |
|---|---|---|---|---|
| S2 | 0.0 (115°)[a] | 4.1 (123°)[a] | 1.6 (118°)[a] | 4.4 (121°)[a] |
| S5 | 0.0 (114°)[a] | 4.1 (123°)[a] | 0.3 (117°)[a] | 4.1 (120°)[a] |
| S6 | 0.0 (114°)[a] | 4.2 (123°)[a] | 0.3 (117°)[a] | 4.2 (119°)[a] |

[a]Ru—S—Ar bond angle given in parenthesis.

The contribution of the high-energy reaction paths (E2 and Z2) in the overall olefin metathesis process can reasonably be expected to be very low, and therefore, for the sake of simplicity and to reduce the computational cost, we have neglected them in the rest of this work.

FIG. 10 shows that the product stereoselectivity may be determined either in the MCB break-up step (TS2) or in the product release step (AC2). In other words, to evaluate the Z-selectivity of a catalyst it is sufficient to calculate only the relative free energies of these two stationary points. Table 3 gives the Gibbs free energy in toluene for $TS2_{E1}$ (the E1-isomer of the TS2 transition state), $AC2_Z$ ($LXX^1RuCH_2$+ Z-product), and $AC2_E$ ($LXX^1RuCH_2$+E-product) relative to $TS2_{Z1}$ (the Z1-isomer of the TS2 transition state, set to zero as a reference).

changes in the energy profile (the one pertaining to $\Delta GAC2_E$) renders the catalytic reaction less dependent on the overall thermodynamics (i.e., the risk of a thermodynamic equilibrium between the Z- and E-product becomes lower) compared to that of O1. The second change (the one pertaining to $\Delta G^‡TS2_{(E1-Z1)}$) renders the formation of the Z-product kinetically more favorable compared to formation of the E-product. Thus, both modifications of the free energy profile of the reaction resulting from replacement of oxygen by sulfur contribute to improving the Z-selectivity of the catalyst. By tuning steric and electronic properties of the $X^1$ ligand, it is possible to modify both the dependence on the

TABLE 2

Relative Gibbs Free energy of the stationary points TS2 and AC2.[a]

| Catalyst[b] | R, R'[c] | $\Delta G^‡TS2_{Z1}$ | $\Delta G^‡TS2_{E1}$ | $\Delta GAC2_Z$ | $\Delta GAC2_E$ | Ru—Y—W angle (°)[d] | Ru—Y—W angle (°)[e] |
|---|---|---|---|---|---|---|---|
| H2 | Me | 0.0 | 0.8 | 1.6 | 0.7 | — | — |
| H2 | n-Bu | 0.0 | 0.4 | 2.1 | 1.4 | — | — |
| O1 | Me | 0.0 | 0.7 | −3.1 | −4.0 | 121 | 135 |
| S1 | Me | 0.0 | 1.5 | −4.6 | −5.5 | 99 | 118 |
| S2 | Me | 0.0 | 1.6 | −6.5 | −7.3 | 98 | 118 |
| S2 | n-Bu | 0.0 | 0.8 | −4.7 | −5.3 | 98 | 118 |
| S3 | Me | 0.0 | 0.9 | −5.2 | −6.1 | 98 | 118 |
| S4 | Me | 0.0 | 1.0 | −9.4 | −10.2 | 99 | 118 |
| S5 | Me | 0.0 | 0.3 | −8.6 | −9.4 | 96 | 117 |
| S6 | Me | 0.0 | 0.3 | −8.8 | −9.6 | 96 | 117 |
| S7 | Me | 0.0 | 2.5 | −8.0 | −8.9 | 93 | 115 |
| S8 | Me | 0.0 | 2.2 | −6.5 | −7.4 | 96 | 116 |
| S9 | Me | 0.0 | 0.6 | −6.7 | −7.6 | 102 | 117 |
| Se1 | Me | 0.0 | 2.5 | −7.4 | −8.3 | 92 | 113 |
| Te1 | Me | 0.0 | 1.5 | −6.2 | −7.1 | 91 | 111 |
| P1 | Me | 0.0 | 1.5 | −6.3 | −7.2 | 101 | 117 |
| As1 | Me | 0.0 | 2.3 | −7.4 | −8.3 | 97 | 114 |
| C1 | Me | 0.0 | −0.3 | −10.7 | −11.6 | 92[f] (122)[g] | 113[f] (119)[g] |
| C2 | Me | 0.0 | −0.3 | −9.2 | −10.1 | 95[f] (113)[g] | 112[f] (118)[g] |
| Os1 | Me | 0.0 | 1.7 | −7.8 | −8.6 | 100 | 117 |
| Os2 | Me | 0.0 | 1.3 | −8.9 | −9.8 | 98 | 116 |

[a]Energies in kilocalories per mole, calculated at 298.15 K with bulk solvent effects (toluene) obtained using PCM.[4] See Scheme 2 for the definition of TS2 and AC2.
[b]The Lewis structure of the 14-electron ruthenium-ethylidene complexes are shown in Chart 1.
[c]R and R' are the substituents on the alkylidene group ($LXX^1Ru$=CHR, see Chart 1), and on the olefinic substrate ($CH_2$=CHR'), respectively.
[d]DFT-optimized geometry of the corresponding methylidene complex.
[e]DFT-optimized geometry of $TS2_{E1}$.
[f]The most acute of the Ru—C—C angles.
[g]The most obtuse of the Ru—C—C angles.

Based on the above arguments we evaluate the Z-selectivity as the Gibbs free energy difference between the E- and Z-isomer in the stationary point having the highest free energy along the reaction path. This stationary point is AC2 when the corresponding value of $\Delta GAC2_E$ given in Table 3 is positive (which is true only for H2, $\Delta GAC2_E$=0.7 kcal/mol) and TS2 when $\Delta GAC2_E$ is negative (true for all the other complexes in Table 3). Consequently the stereoselectivity is determined by $\Delta GAC2_{(E-Z)}$ for the complex H2 and $\Delta G^*TS2_{(E1-Z1)}$ for all the other complexes in Table 3

Complexes O1 and S1 differ only by the nature of the bridgehead atom (i.e., the atom of the ligand which is directly bound to the central metal atom) in the $X^1$ ligand, namely oxygen in O1 and sulfur in S1, thus a comparison of these two complexes gives an idea as to the gain in Z-stereoselectivity that can be expected when an oxygen-based ligand is replaced by a sulfur-based ligand. DFT calculations (Table 2) show that the product release becomes more facile (($\Delta GAC2_E)_{S1}$=−5.5 kcal/mol, compared to ($\Delta GAC2_E)_{O1}$=−4.0 kcal/mol) and the MCB break-up step for the Z1-path more favored (($\Delta G^‡TS2_{(E1-Z1)})_{S1}$=1.5 kcal/mol, compared to ($\Delta G^‡TS2_{(E1-Z1)})_{O1}$=0.7 kcal/mol). The first of these termodynamic stability of the product and the relative, rate-determining barrier height for formation of the two isomers. For example, 2,6-dichlorothiophenolate (the $X^1$ ligand of S2) is predicted to favor, thermodynamically as well as kinetically, formation of Z-product slightly more than does the closely related 2,3,4,5,6-pentachlorothiophenolate ligand (of S1). The best ligands (among those investigated) are predicted to be 2,4,6-triphenylthiophenolate (of S7) and 2,4,6-triphenylselenophenolate (of Se1). The corresponding catalysts have the most favorable kinetic profile for formation of the Z-product (($\Delta G^‡TS2_{(E1-Z1)})_{S7}$= ($\Delta G^‡TS2_{(E1-Z1)})_{SE1}$=2.5 kcal/mol) and also appear to be among the catalysts less prone to thermodynamic product control (($\Delta GAC2_E)_{S7}$=−8.9 kcal/mol, compared to ($\Delta GAC2_E)_{SE1}$=−8.3 kcal/mol). Finally, increasing the size of the substrate (1-hexene vs. 1-propene) renders the product release slightly more difficult (see Table 2: ($\Delta GAC2_E)_{H2}$=1.4 kcal/mol, and ($\Delta GAC2_E)_{S2}$=−5.3 kcal/mol when R=R'=n-Bu, compared to ($\Delta GAC2_E)_{H2}$=0.7 kcal/mol and ($\Delta GAC2_E)_{S2}$=−7.3 kcal/mol when R=R'=Me), and makes the Z- and Z1-paths of both H2 (see Table 2: ($\Delta G^‡TS2_{(E1-Z1)})_{H2}$=0.4 kcal/mol when R=R'=n-

Bu, compared to $(\Delta G^{\ddagger}TS2_{(E1-Z1)})_{H2}=0.8$ kcal/mol when R═R'═Me), and S2 (see Table 2: $(\Delta G^{\ddagger}TS2_{(E1-Z1)})_{S2}=0.8$ kcal/mol when R═R'═n-Bu, compared to $(\Delta G^{\ddagger}TS2_{(E1-Z1)})_{S2}=1.6$ kcal/mol when R═R'═Me), less favored. Thus, the effects on the free energy profile arising from changing the substrate are essentially systematic, although somewhat more pronounced for S2 (see Table 2: $(\Delta GAC2_E)_{(R=R'=n-Bu)} - (\Delta GAC2_E)_{(R=R'=Me)}=2.0$ kcal/mol, and $(\Delta G^{\ddagger}S2_{(E1-Z1)})_{(R=R'=n-Bu)} - (\Delta G^{\ddagger}TS2_{(E1-Z1)})_{(R=R'=Me)}=-0.8$ kcal/mol) than for H2 (see Table 2: $(\Delta GAC2_E)_{(R=R'=n-Bu)} - (\Delta GAC2_E)_{(R=R'=Me)}=0.7$ kcal/mol, and $(\Delta G^{\ddagger}TS2_{(E1-Z1)})_{(R=R'=n-Bu)} - (\Delta G^{\ddagger}TS2_{(E1-Z1)})_{(R=R'=Me)}=-0.4$ kcal/mol). These results for H2 and S2 suggest that the general trend in stereoselectivity, as calculated for the metathesis homocoupling of propene (shown in Table 2), is valid also for other substrates.

Computational Details

Geometry Optimizations.

All geometry optimizations were performed using the generalized gradient approximation (GGA) functional PBEPBE (22) as implemented in the Gaussian 03 suite of programs. (23) The default criteria were adopted for the self-consistent-field (SCF) convergence. Numerical integrations were performed using the "ultrafine" (pruned, 99 radial shells and 590 angular points per shell) grid in a combination with "Tight" geometry optimization convergence criteria (Maximum Force=0.000015 Hartree/Bohr, RMS Force=0.000010 Hartree/Bohr, Maximum Displacement=0.000060 Å, RMS Displacement=0.000040 Å). Wavefunction stability tests were routinely carried out. All stationary points were characterized by the eigenvalues of the analytically calculated Hessian matrix. Thermochemical corrections at 298.15 K were computed within the harmonic-oscillator, rigid-rotor, and ideal-gas approximations.

The Dunning double-ζ basis set (24), contracted (4s)/[2s], was used for hydrogen. The Stuttgart 2-electron (first row), 10-electron (second row), 28-electron (third row), and 46-electron (Te) effective core potentials (ECPs) were used with accompanying (4s2p)/[2s2p]-contracted valence basis sets for carbon, nitrogen, phosphorous, and arsenic and (4s5p)/[2s3p]-contracted valence basis sets for oxygen, fluorine, sulfur, chlorine, selenium, and tellurium. A single set of polarization d functions (25) was added for all the p-block elements resulting in a 4s2p1d)/[2s2p1d]-contracted valence basis set for C, N, P, and As and a (4s5p1d)/[2s3p1d]-contracted valence basis set for O, F, S, Cl, Se, and Te. Finally, for ruthenium (osmium), the Stuttgart 28-electron (60-electron) relativistic effective core potentials (ECP) were used with accompanying (8s,7p,6d)/[6s,5p,3d]-contracted basis sets (26).

Conformational Issues.

Ligands and complexes were chosen in such a way as to easily handle conformational issues. Most of the ligands are symmetrically substituted and have a relatively low number of rotatable bonds. Moreover, all these ligands show the same or at the most only a couple of different conformations in complexes for which the X-ray structure is available (27). Therefore, the number of reasonably low-lying conformers is expected to be very limited in all cases.

Conformational searches were performed using the Merck Molecular Force Field (MMFF94) (28) as well as a semiempirical method (PM3) (29) implemented in Spartan'08 (30). In these conformational searches, bond distances and angles involving the metal center were constrained to the positions obtained in a preliminary DFT geometry optimization of the same or of a closely related complex. In cases where the most stable conformers found by MMFF94 and PM3 methods were different, both geometries were optimized using DFT, and the conformer giving the thus calculated lowest Gibbs free energy was chosen.

Single Point (SP) DFT Energy Evaluations.

The total energy and the electronic properties were re-evaluated at the optimized geometry, using the wB97XD (31) density functional as implemented in the Gaussian 09 suite of programs (32).

The basis sets used in the SP energy calculations were improved compared to those used in geometry optimization. For hydrogen, the Dunning triple-ζ basis set (33) was augmented by a diffuse s function ($\alpha_s$=0.043152, obtained even-temperedly), and a polarization p function ($\alpha_p$=1.00), resulting in (5s,1p)/[4s,1p]-contracted basis set. The basis sets of the p-block elements (25) were decontracted to triple-ζ quality, and extended with a single set of diffuse p functions (34) for those elements (C, N, P, and As) that did not already have such functions in the geometry optimization basis sets. Moreover, a single set of diffuse s functions, obtained even-temperedly, were added, resulting in (5s,5p,1d)/[4s,4p,1d]-contracted basis sets. Finally, for ruthenium and osmium, two polarization f functions (26b) were added to the basis sets described above. The resulting (8s,7p,6d,2f) basis set was contracted to [7s,6p,4d,2f] (26).

Solvent effects for toluene were estimated by the polarizable continuum model (PCM) (37) using united-atom Kohn-Sham (UAKS) radii to construct the solvent cavity.

2. EXPERIMENTAL

Reactions were performed under dry argon atmosphere using Schlenk techniques, unless otherwise stated. Toluene, tetrahydrofuran (THF), hexane and diethyl ether (Et$_2$O) were dried using an MBraun solvent purification system ("Grubbs' column") and degassed before use. Pentane was distilled over NaK alloy and degassed before use. (H$_2$IMes)(Cl)$_2$(Py)$_2$Ru═CHPh [H$_2$IMes=1,3-dimesityl-4,5-dihydroimidazol-2-ylidene, Py=pyridine] (18) and 1,10-bis(allyloxy)-decane (35) were prepared according literature procedures. Allylacetate, 1-hexene, and 1-octene were purchased from Sigma-Aldrich and degassed before use. 1-Octene and 1-hexene were additionally dried over molecular sieves (4 Å). All the other chemicals were purchased from Sigma-Aldrich, Alfa Aesar, Acros, TCI Europe and used as received.

Potassium thiophenolates used as starting material in examples 1-4 were prepared according the following scheme:

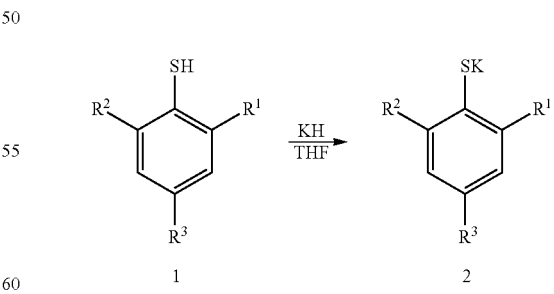

a) $R^1 = R^2 = Cl; R^3 = H$
b) $R^1 = R^2 = Me; R^3 = H$
c) $R^1 = R^2 = R^3 = Me$
d) $R^1 = R^2 = R^3 = Ph$

A solution of the corresponding thiophenol (5 mmol) in THF (30 mL) was dropwise added to a suspension of KH (5.3 mmol) in THF (10 mL), The mixture was stirred at room temperature for 30 minutes, followed by additional stirring for 15 minutes at 50° C.

For the salts which are soluble in THF (2a, 2b, and 2c), the resulting solution was filtered, and the filtrate evaporated to leave the corresponding crude potassium thiophenolates as white solids, while for 2d the solvent was removed under reduced pressure and the yellowish-pale solid was washed with hexane and dried under vacuum. The salts thus obtained were used without further purification. The quality of the product was evaluated by $^1$H-NMR spectroscopy, which showed in all cases the disappearance, or only traces of, the proton peak corresponding to the thiol group (SH).

NMR spectra were recorded on a Bruker Biospin DPX400 spectrometer. The chemical shifts are reported relative to the residual solvent peaks.

DART-MS spectra were recorded by means of a DART-100 ion source from IonSense Inc. (Saugus, Mass., USA) interfaced to an AccuTOF™ atmospheric ionization mass spectrometer from JEOL USA, Inc. (Peabody, Mass., USA). X-ray diffraction measurements were performed on a Bruker Apex Ultra TXS, rotating anode, CCD instrument doing 0.3-0.5 degree ω scans over 182° in four orthogonal φ-settings. The samples were cooled using a $N_2$ blower, series 700 from Oxford Cryosystem. Apart from geometrical corrections, numerical absorption correction by face indexing with Gaussian quadrature integration, and semi-empirical incident beam correction were applied.

Example 1

Preparation of Ruthenium Complex 3a

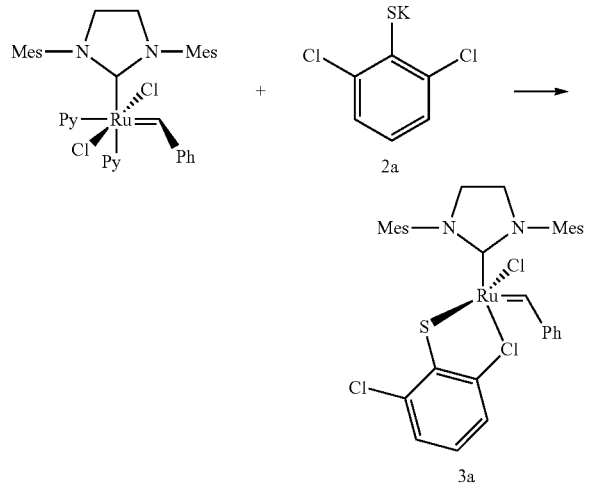

$(H_2IMes)(Cl)_2(Py)_2Ru$=CHPh (95.1 mg, $1.31·10^{-1}$ mmol) and potassium 2,6-dichlorothiophenolate (60.2 mg, $2.77·10^{-1}$ mmol) 2a were suspended in 4 mL toluene and 1 mL THF and the mixture stirred at 35° C. for 45 minutes. During this time the color of the mixture turned from light green to dark green. The mixture was filtered through a cannula to remove precipitated KCl, unreacted potassium 2,6-dichlorothiophenolate and other insoluble compounds. The volume of solvent was reduced in vacuo to about half, and then 10 mL $Et_2O$ was added to precipitate the crude product as a green powder. Further purification was obtained by dissolving the crude in a minimum of THF, cooling to −60° C., and precipitating the product with $Et_2O$ (10 mL). The solid product was isolated by filtration, washed twice with small portions (2-3 mL) of cold $Et_2O$ and dried under reduced pressure to give the complex 3a in a yield of 46.0% (42.8 mg). $^1$H NMR (400.13 MHz, $CDCl_3$): δ=16.54 (s, 1H, Ru=CH), 6.6-7.4 (m, 12H, Ar), 3.97 (s, 4H, NCH—CH—N), 2.51 (s, 12H, (ortho) Ar—$CH_3$), 2.11 (s, 6H, (para) Ar—$CH_3$); $^{13}$C{1H} NMR (100.31 MHz, $CDCl_3$): δ=301.70, 207.20, 152.08, 147.55, 138.36, 137.86, 136.86, 136.35, 130.62, 129.48, 129.35, 127.49, 126.71, 122.38, 52.19, 21.10, 19.60. MS (DART), m/z: 711.07187 (M+H)$^+$; calc. for $C_{34}H_{36}Cl_3N_2SRu$: 711.07083.

Example 2

Preparation of Ruthenium Complex 4b

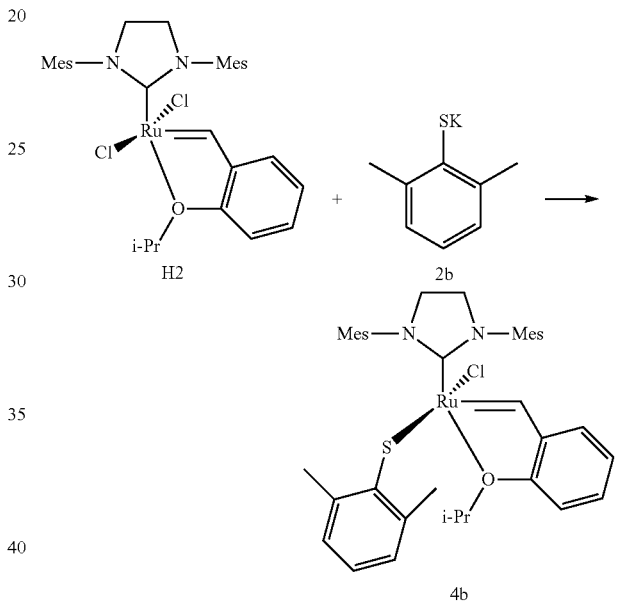

Hoveyda-Grubbs second generation catalyst H2 (104 mg, 0.16 mmol) and potassium 2,6-dimethylbenzenethiolate (34 mg, 0.19 mmol) 2b were transferred to a 25 mL Schlenk flask, followed by addition of 4 mL of toluene and 1 mL THF under argon. Then the mixture was stirred vigorously at 20° C. for 30 min. During this time the color of the mixture turned from light green to a slightly darker green. The reaction mixture was filtered, and the volume of the filtrate reduced to about 3 mL. Hexane (15 mL) was added to the filtrate to precipitate the product 4b as red/orange-brown micro-crystals (86.3 mg, 71%).

Crystals for X-ray diffraction analysis (see FIG. 12 and Table 4) were prepared by dissolving a sample in a minimal amount of toluene, upon which a layer of hexane was added. Red-brown crystals were formed over a period of 3 days at room temperature.

$^1$H NMR (400.13 MHz, $CDCl_3$): δ=14.90 (s, 1H), 7.22 (m, 1H), 7.10 (s, 2H), 7.06 (s, 2H), 6.80-6.73 (m, 2H), 6.66 (t, J=7.2 Hz, 1H), 6.16 (d, J=8.0 Hz, 1H), 4.15 (m, 4H), 3.83 (sep, J=6.16 Hz, 1H), 2.62 (s, 6H), 2.54 (s, 6H), 2.42 (s, 6H), 2.32 (br s, 3H), 1.8 (d, J=5.6 Hz, 3H), 0.89 (d, J=6.4 Hz, 3H), 0.80 (br s, 3H). $^{13}$C NMR (100.6 MHz, $CDCl_3$): δ=271.29, 211.87, 151.57, 145.12, 142.30 (br), 141.67, 139.25, 138.90, 138.75, 137.40 (br), 129.74, 129.43, 127.32, 126.61, 124.43, 123.12, 122.34, 114.19, 74.99, 52.15, 21.55, 21.45, 21.43, 20.07 (br).

A corresponding ORTEP-style diagram of 4b is shown in FIG. 12. Selected geometrical parameters: Ru1-C9=1.846 Å, Ru1-S1=2.285 Å, Ru1-Cl1=2.364 Å, Ru1-O1=2.298 Å, Ru1-S1-C1=113.67°, Cl1-Ru1-S1=150.75°.

TABLE 4

Crystal data and structure refinement for complex 4b.

| | |
|---|---|
| Empirical formula | $C_{39}H_{47}ClN_2ORuS$ |
| Formula weight | 728.37 |
| Temperature (K) | 123(2) |
| Crystal system | Triclinic |
| Space group | P-1 |
| Unit cell dimensions | A = 10.8713(10) Å  α = 84.505(1)° |
| | B = 10.9181(10) Å  β = 88.770(1)° |
| | C = 16.1043(15) Å  γ = 67.994(1)° |
| V (Å$^3$) | 1763.9(3) |
| Z | 2 |
| D(calculated) | 1.371 Mg/m$^3$ |
| Absorption coefficient | 0.612 mm$^{-1}$ |
| F(000) | 760 |
| Reflections collected | 31898 |
| Crystal size (mm$^3$) | 0.58 × 0.40 × 0.12 |
| Index ranges | −16 ≤ h ≤ 16, |
| | −16 ≤ k ≤ 16, |
| | −23 ≤ l ≤ 23 |
| Goodness-of-fit on F$^2$ | 1.163 |
| Final R, wR$^2$ (for I > 2σ) | 0.0356, 0.0929 |
| R, wR$^2$ (all data) | 0.0378, 0.0940 |
| Largest diff. peak and hole (e · Å$^{-3}$) | 1.377 and −1.287 |
| Empirical formula | $C_{39}H_{47}ClN_2ORuS$ |
| Formula weight | 728.37 |

Example 3

Preparation of Ruthenium Complex 4c

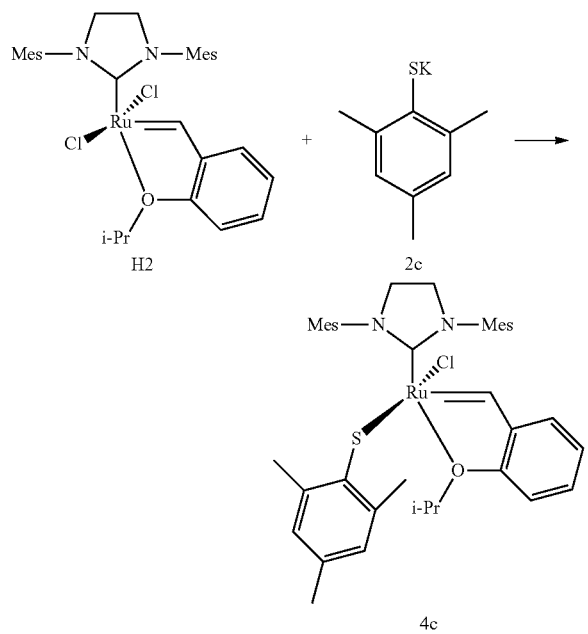

Hoveyda-Grubbs second generation catalyst (150 mg, 0.24 mmol) and potassium 2,4,6-trimethylbenzenethiolate 2c (59 mg, 0.31 mmol) were transferred to a 25 mL Schlenk flask, followed by addition of 5 mL of benzene and 1 mL of THF under argon. Then the mixture was stirred vigorously at 20° C. for 30 min. During this time the color of the mixture turned from light green to dark green. The reaction mixture was filtered, and the volume of the filtrate reduced to about 3 mL. Hexane (15 mL) was then added to the dark-green solution under stirring to precipitate the ruthenium complex 4c as a dark green powder (98.5 mg, 55.3%). Further purification was accomplished by dissolving the product in benzene and precipitating with hexane. Crystals for X-ray crystal structure determination were grown by slow diffusion of pentane to a concentrated solution of 4c in fluorobenzene, see FIG. 13 and Table 5.

$^1$H NMR (400.13 MHz, CDCl$_3$): δ=14.89 (s, 1H), 7.20 (m, 1H), 7.09 (s, 2H), 7.05 (s, 2H), 6.78-6.73 (m, 2H), 6.57 (br s, 1H), 6.14 (d, 1H), 5.99 (br s 1H), 4.13 (m, 4H), 3.95 (sep, 1H), 2.62 (s, 6H), 2.54 (s, 6H), 2.42 (s, 6H), 2.28 (br s, 3H), 2.03 (d, J=6.1 Hz, 3H), 0.92 (d, J=6.1 Hz, 3H), 0.81 (br s, 3H). $^{13}$C NMR (100.6 MHz, CD$_2$Cl$_2$): δ=269.24, 211.58, 151.83, 145.22, 139.26, 138.89, 138.82, 138.16, 133.95, 129.72, 129.39, 127.54, 127.30, 122.75, 122.40, 114.07, 75.20, 53.84, 52.25, 21.40, 21.20, 21.17, 20.79, 19.89.

A corresponding ORTEP-style diagram of 4c is shown in FIG. 13. Selected geometrical parameters: Ru1-C16=1.842 Å, Ru1-S1=2.338 Å, Ru1-Cl1=2.375 Å, Ru1-O1=2.236 Å, Ru1-S1-C1=107.66°, Cl1-Ru1-S1=159.61°.

TABLE 5

Crystal data and structure refinement for complex 4c.

| | |
|---|---|
| Empirical formula | $C_{40}H_{49}ClN_2ORuS \cdot 0.5(C_6H_5F)$ |
| Formula weight | 789.94 |
| Temperature (K) | 123(2) |
| Crystal system | Monoclinic |
| Space group | P2(1)/C |
| Unit cell dimensions | a = 21.2851(5) Å  α = 90° |
| | b = 12.8247(3) Å  β = 94.932(1)° |
| | c = 14.1960(3) Å  γ = 90° |
| V (Å$^3$) | 3860.80(15) |
| Z | 4 |
| D(calculated) | 1.359 Mg/m$^3$ |
| Absorption coefficient | 0.567 mm$^{-1}$ |
| F(000) | 1650 |
| Reflections collected | 69897 |
| Crystal size (mm$^3$) | 0.40 × 0.22 × 0.22 |
| Index ranges | −31 ≤ h ≤ 31, |
| | −18 ≤ k ≤ 18, |
| | −20 ≤ l ≤ 20 |
| Goodness-of-fit on F$^2$ | 1.071 |
| Final R, wR$^2$ (for I > 2σ) | 0.0249, 0.0698 |
| R, wR$^2$ (all data) | 0.0264, 0.0711 |
| Largest diff. peak and hole (e · Å$^3$) | 1.008 and −0.418 |
| Reflections collected | 69897 |

Example 4

Preparation of Ruthenium Complex 4d

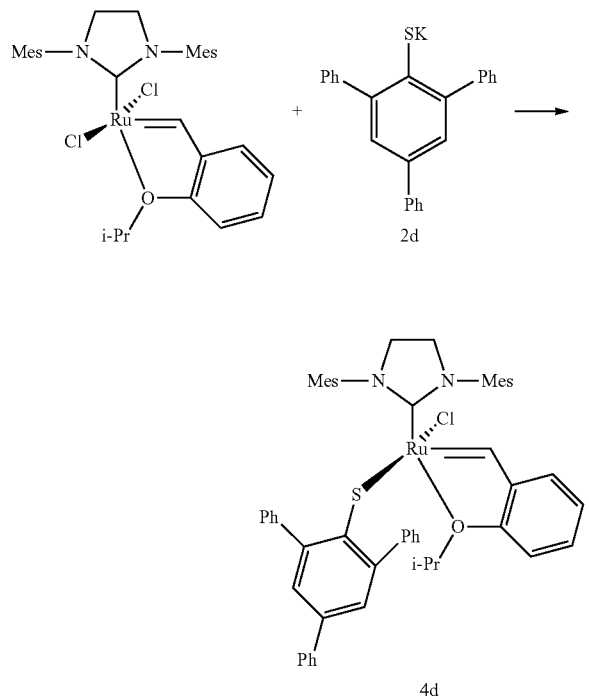

Potassium 2,4,6-triphenylthiophenolate 2d (53 mg, 0.14 mmol) was transferred to a 25 mL Schlenk flask, followed by addition of 5 mL of THF under argon, and the mixture was stirred vigorously and heated at 55° C. Hoveyda-Grubbs second generation catalyst (82 mg, 0.13 mmol) dissolved in toluene (1 mL) was then added, and the mixture stirred at 55° C. for 2.5 h. The solvents were then removed in vacuo, and the product was redissolved in 6 mL Et$_2$O. Following filtration, 3 mL of hexane was added, and the mixture cooled to −40° C., causing precipitation of impurities. After allowing solids to settle, the solution was filtered, and the solvents removed in vacuo to yield the crude 4d complex as a green powder (50.7 mg, 42%). $^1$H NMR (400.13 MHz, C$_6$D$_6$): δ=14.50 (s, 1H), 7.80 (d, J=6.4 Hz, 2H), 7.47 (t, J=6.7 Hz, 2H), 7.42-7.34 (m, 2H), 7.31-7.21 (m, 3H), 7.11 (t, J=7.2 Hz, 3H), 7.08-7.00 (m, 3H), 6.99-6.90 (m, 3H), 6.87 (s, 2H), 6.79-6.60 (m, 4H), 6.15 (d, J=8.2 Hz, 2H), 4.15 (sept, J=6.1 Hz, 1H), 3.38-3.20 (m, 4H), 2.47 (s, 6H), 2.38 (s, 6H), 2.29 (s, 6H), 1.15 (d, J=6.1 Hz, 3H), 0.59 (d, J=6.1 Hz, 3H).

$^{13}$C NMR (100.6 MHz, CD$_2$Cl$_2$): δ=276.55, 210.42, 153.68, 146.72, 138.75, 138.16, 131.23, 129.58, 129.12, 128.97, 128.75, 128.31, 127.87, 127.77, 127.50, 127.23, 127.01, 125.83, 122.65, 121.72, 113.38, 76.15, 53.87, 51.98, 21.54, 21.25, 20.83, 19.92, 19.04. MS (DART), m/z: 928.27512 (M+H)$^+$; calc. for C$_{55}$H$_{56}$OClN$_2$SRu: 928.27671.

Example 5

Metathesis Homocoupling of Allylacetate

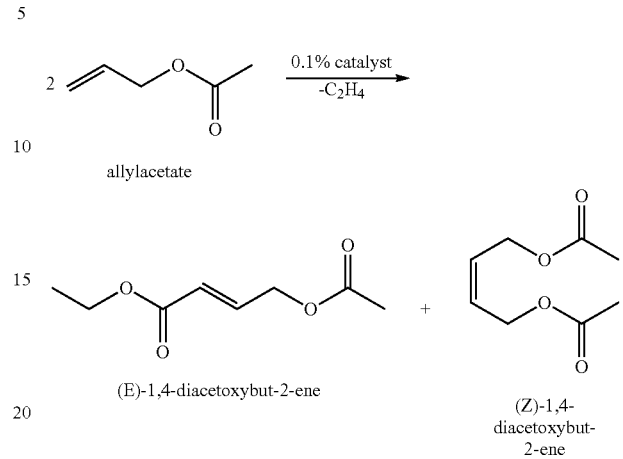

A 25 mL Schlenk flask was charged with the catalyst (1.6×10$^{-3}$ mmol) and then 174 µL of allylacetate was added to the flask under argon. The mixture was stirred at 60° C. for 2 hours. The reaction was quenched by filtration through a plug of silica gel (~2 cm) packed in a Pasteur pipette using hexane as eluent. An aliquot of the filtrate (10 µL) was diluted in 0.5 mL of CDCl$_3$ and used to evaluate the percentage of conversion by 1H NMR spectroscopy. The remaining solution was concentrated using a stream of nitrogen and the residual, containing a mixture of E- and Z-1,4-diacetoxybut-2-ene, was dissolved in CDCl$_3$ and analyzed by $^1$H NMR. The percentage of Z-1,4-diacetoxybut-2-ene in this mixture was determined by integrating the multiplets corresponding to the two vinylic protons at 5.86 ppm (E-isomer) and 5.75 ppm (Z-isomer), respectively.

TABLE 6

Metathesis homocoupling of allylacetate

| entry | catalyst | mol % | time (h) | temp. (° C.) | % conv. | % Z |
|---|---|---|---|---|---|---|
| 1 | H2 | 0.1 | 2 | 60 | 83 | 13 |
| 2 | 3a | 0.1 | 2 | 60 | 26 | 68 |
| 3 | 4b | 0.1 | 2 | 60 | 44 | 35 |
| 4 | 4c | 0.1 | 2 | 60 | 54 | 35 |
| 5 | 4d | 0.1 | 2 | 60 | 19 | 77 |

Example 6

Metathesis Homocoupling of 1-hexene

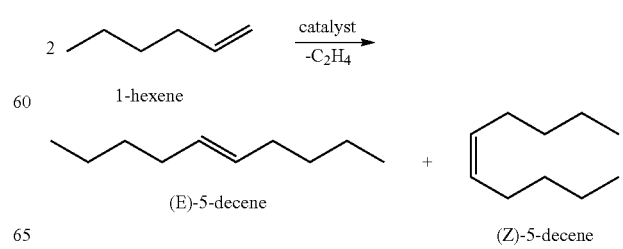

A 25 mL Schlenk flask was charged with the catalyst (3.2×10⁻³ mmol) and then 0.4 mL of 1-hexene was added to the flask under argon. The mixture was stirred at 40° C. for 2 hours. The reaction was quenched by filtration through a plug of silica gel (~2 cm) packed in a Pasteur pipette using pentane as eluent. An aliquot of the filtrate (10 µL) was diluted in 0.5 mL of CDCl₃ and used to evaluate the percentage conversion by 1H NMR spectroscopy. The remaining solution was concentrated using a stream of nitrogen and an aliquot of the residual, containing almost exclusively a mixture of E- and Z-decene, was dissolved in CDCl₃ and analyzed by $^1$H NMR. The percentage of Z-decene in this mixture was determined by integrating the multiplets corresponding to the two vinylic protons at 5.39 ppm (E-isomer) and 5.35 ppm (Z-isomer) respectively. The chemical shifts of the two isomers were determined by recording the $^1$H NMR spectra of the commercially available compounds (E)-5-decene (Sigma-Aldrich) and (Z)-5-decene (TCI Europe)) in CDCl₃.

TABLE 7

Metathesis homocoupling of 1-hexene

| entry | catalyst | mol % | solvent | sub. conc. (M) | time (min) | temp. (° C.) | % conv. | % Z |
|---|---|---|---|---|---|---|---|---|
| 1 | H2 | 0.1 | — | — | 120 | 60 | 92 | 16 |
| 2 | 3a | 0.1 | — | — | 120 | 60 | 72 | 36 |
| 3 | 3a | 0.1[a] | — | — | 120 | 60 | 63 | 44 |
| 4 | 3a | 0.1 | THF | 3 | 40 | 40 | 45 | 52 |
| 5 | 3a | 0.1 | THF | 3 | 120 | 40 | 79 | 33 |
| 6 | 4b | 0.1[b] | — | — | 120 | 40 | 49 | 49 |
| 7 | 4b | 0.1 | — | — | 120 | 60 | 94 | 19 |
| 8 | 4c | 0.1[c] | — | — | 120 | 40 | 20 | 46 |
| 9 | 4d | 0.1 | — | — | 120 | 40 | 92 | 59 |
| 10 | 4d | 0.01 | — | — | 120 | 60 | 40 | 85 |

[a]Additive: 5 equivalents of potassium salt 2a.
[b]Additive: 5 equivalents of potassium salt 2b.
[c]Additive: 5 equivalents of potassium salt 2c.

Example 7

Metathesis Homocoupling of 1-octene

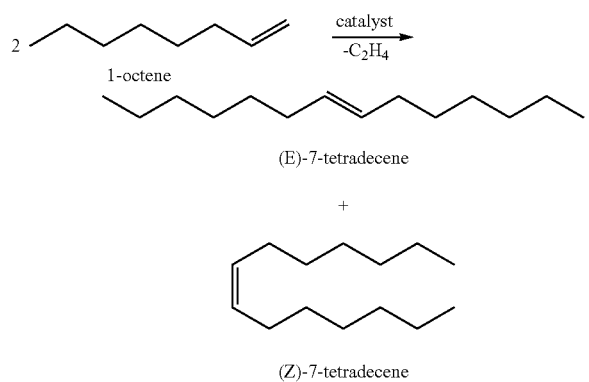

A 25 mL Schlenk flask was charged with the catalyst (3×10⁻³ mmol) and then 470 µL of 1-octene and 530 µL of THF were added to the flask under argon. The mixture was stirred at 60° C. for 2 hours. The reaction was quenched by filtration through a plug of silica gel (~5 cm) packed in a Pasteur pipette using pentane as eluent. An aliquot of the filtrate (10 µL) was diluted in 0.5 mL of CDCl₃ and used to evaluate the percentage conversion by 1H NMR spectroscopy. The remaining solution was concentrated using a stream of nitrogen and an aliquot of the residual, containing almost exclusively a mixture of (E)- and (Z)-7-tetradecene, was dissolved in CDCl₃ and analyzed by $^1$H NMR. The percentage of (Z)-7-tetradecene in this mixture was determined by integrating the multiplets corresponding to the two vinylic protons at 5.39 ppm (E-isomer)(38) and 5.35 ppm (Z-isomer) respectively.

TABLE 8

Metathesis homocoupling of 1-octene

| entry | catalyst | mol % | solvent | Sub. conc. (M) | time (h) | temp. (° C.) | % conv. | % Z |
|---|---|---|---|---|---|---|---|---|
| 1 | H2 | 0.1 | THF | 3 | 1 | 40 | >99 | 18 |
| 2 | 3a | 0.1 | THF | 3 | 1 | 40 | 55 | 42 |
| 3 | 4d | 0.1 | THF | 3 | 1 | 40 | 64 | 85 |

Example 8

Ring Closing Metathesis of 1,10-Bis(Allyloxy)-Decane

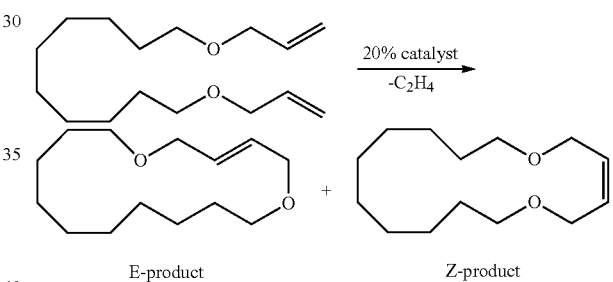

E-product       Z-product

The catalyst (0.016 mmol) and 1,10-bis(allyloxy)-decane (20.4 mg, 0.08 mmol) were dissolved in 10 mL of toluene under argon. The solution was stirred at 65° C. for 5 hours. The solvent was removed under reduced pressure and the product (a mixture of E- and Z-isomers) was isolated by column chromatography (silica gel, 1:19 solvent mixture of diethyl ether/hexane). The percentage of the Z-isomer in this mixture was determined using $^1$H NMR (CDCl₃) by integrating the two doublets corresponding to the four allylic protons at 4.05 ppm (Z-isomer) and 3.98 ppm (E-isomer) respectively (35).

TABLE 9

Ring closing metathesis of 1,10-bis(allyloxy)-decane

| entry | catalyst | mol % | solvent | Sub. conc. (10⁻³M) | time (h) | temp. (° C.) | % conv. | % Z |
|---|---|---|---|---|---|---|---|---|
| 1[a] | G1[b] | 20 | toluene | 21 | 24 | r.t. | 28[c] | 10 |
| 2 | H2[c] | 20 | toluene | 8 | 5 | 65 | 95[d] | 3 |
| 3 | 3a | 20 | toluene | 8 | 5 | 65 | 47[d] | 25 |

[a]Result taken from the literature.[18]
[b]Grubbs first generation catalyst.
[c]Hoveyda-Grubbs second generation catalyst.
[c]Isolated yield.
[d]Estimated by $^1$H NMR

3. VALIDATION OF THE COMPUTATIONAL MODEL

With the aim to validate the computational model, we have correlated the predicted Z-selectivities for the metathesis homocoupling of propene as defined in section 1.4 (i.e. $\Delta GAC2_{(E\text{-}Z)}$ in kcal/mol for H2, and $\Delta G^{\ddagger}TS2_{(E1\text{-}Z1)}$ in kcal/mol for the other catalysts, see Table 3), with the percentage of Z-product obtained in the actual (experimental) metathesis homocoupling of allylacetate (Table 6). These data are given in Table 12.

The correlation between the predicted and experimentally observed Z-selectivity is convincing ($R^2$=0.98), suggesting that a good deal of trust can be put in the computational predictions so far not followed up by experiments.

Based on this correlation between the computational and experimental data we have constructed a linear model to estimate the experimental Z-selectivity for all ruthenium and osmium alkylidene complexes investigated by means of DFT calculations.

TABLE 12

Predicted and experimental Z-selectivities for the metathesis homocoupling of allylbenzene.

| Catalyst[a] | R, R'[b] | Ru—Y—W angle (°)[c] | Ru—Y—W angle (°)[d] | $\Delta G^{\ddagger}TS2_{(E1\text{-}Z1)}$[e] | Expt. % Z | Predicted % Z[f] |
|---|---|---|---|---|---|---|
| H2 | Me | — | — | −0.9 | 13 | 13 |
| O1 | Me | 121 | 135 | 0.7 | | 44 |
| S1 | Me | 99 | 118 | 1.5 | | 61 |
| S2 (3a) | Me | 98 | 118 | 1.6 | 68 | 62 |
| S3 | Me | 98 | 118 | 0.9 | | 47 |
| S4 | Me | 99 | 118 | 1.0 | | 50 |
| S5 (4b) | Me | 96 | 117 | 0.3 | 35 | 37 |
| S6 (4c) | Me | 96 | 117 | 0.3 | 35 | 36 |
| S7 (4d) | Me | 93 | 115 | 2.5 | 77 | 80 |
| S8 | Me | 96 | 116 | 2.2 | | 73 |
| S9 | Me | 102 | 117 | 0.6 | | 41 |
| Se1 | Me | 92 | 113 | 2.5 | | 81 |
| Te1 | Me | 91 | 111 | 1.5 | | 61 |
| P1 | Me | 101 | 117 | 1.5 | | 60 |
| As1 | Me | 97 | 114 | 2.3 | | 76 |
| C1 | Me | 92[g] (122)[h] | 113[g] (119)[h] | −0.3 | | 24 |
| C2 | Me | 95[g] (113)[h] | 112[g] (118)[h] | −0.3 | | 25 |
| Os1 | Me | 100 | 117 | 1.7 | | 63 |
| Os2 | Me | 98 | 116 | 1.3 | | 57 |

[a]The Lewis structures of the 14-electron ruthenium-ethylidene complexes are shown in Chart 1. In cases where two labels are given, the second (given in parenthesis) pertains to the label used for the synthesized and tested catalyst.
[b]R and R' are the substituents on the alkylidene group (LXX$^1$Ru=CHR, see Chart 1), and on the olefinic substrate (CH$_2$=CHR') respectively.
[c]DFT-optimized geometry of the corresponding methylidene complex.
[d]DFT-optimized geometry of TS2$_{E1}$.
[e]For catalyst H2 $\Delta GAC2_{(E\text{-}Z)}$ has been used instead of $\Delta G^{\ddagger}TS2_{(E1\text{-}Z1)}$, see section 1.4 for details. Energies in kilocalories per mole, calculated at 298.15 K with bulk solvent effects (toluene) obtained using PCM.$^4$
[f]% of Z-product as predicted by the linear regression model.
[g]The most acute of the Ru—C—C angles.
[h]The most obtuse of the Ru—C—C angles.

REFERENCES (1) Hoveyda, A. H.; Zhugralin, A. R., *Nature* 2007, 450, 243;
(2) Grubbs, R. H., *Adv. Synth. Catal.* 2007, 349, 23 and 34;
(3) Thayer, A. M., *Chem. Eng. News* 2007, 85, 37;
(4) Fürstner, A.; Mathes, C.; Lehmann, C. W., *Chem. Eur. J.* 2001, 7, 5299;
(5) Gradillas, A.; Perez-Castells, J., *Angew. Chem. Int. Ed.* 2006, 45, 8086;
(6) Fürstner, A.; Langemann, K., *Synthesis-Stuttgart* 1997, 792;
(7) Fürstner, A.; Rumbo, A., *J. Organomet. Chem.* 2000, 65, 2608; Fürstner, A.; Seidel, G., *J. Organomet. Chem.* 2000, 606, 75;
(8) Fürstner, A.; Guth, O.; Rumba, A; Seidel, G., *J. Am. Chem. Soc.* 1999, 121, 11108;
(9) Jakubec, P.; Cockfield, D. M.; Dixon, D. J., *J. Am. Chem. Soc.* 2009, 131, 16632;
(10) Trnka, T. M.; Grubbs, R. H., *Acc. Chem. Res.* 2001, 34, 18;
(11) Lee, C. W.; Grubbs, R. H., *Org. Lett.* 2000, 2, 2145;
(12) Malcolmson, S. J.; Meek, S. J.; Sattely, E. S.; Schrock, R. R.; Hoveyda, A. H., *Nature* 2008, 456, 933;
(13) Ibrahem, I.; Yu, M.; Schrock, R. R.; Hoveyda, A. H., *J. Am. Chem. Soc.* 2009, 131, 3844;
(14) Flook, M. M.; Jiang, A. J.; Schrock, R. R.; Muller, P.; Hoveyda, A. H., *J. Am. Chem. Soc.* 2009, 131, 7962;
(15) Jiang, A. J.; Zhao, Y.; Schrock, R. R.; Hoveyda, A. H., *J. Am. Chem. Soc.* 2009, 131, 16630;
(16) Blacquiere, J. M.; McDonald, R.; Fogg, D. E.; *Angew. Chem. Int. Ed.* 2010, 49, 3807; Torker, S.; Muller, A.; Sigrist, R.; Chen, P., *Organometallics* 2010, 29, 2735;
(17) Volland, M. A. O.; Rominger, F.; Eisenträger, F.; Hofmann, P., *J. Organomet. Chem.* 2002, 641, 220;
(18) Sanford, M. S.; Love, J. A.; Grubbs, R. H. *Organometallics* 2001, 20, 5314;
(19) Amoroso, D.; Snelgrove, Jennifer L.; Conrad, Jay C.; Drouin Samantha D.; Yap, Glenn P. A.; Fogg, Deryn E., *Adv. Synth. Catal.* 2002, 344, 757;
(20) Conrad, J. C.; Yap, G. P. A.; Fogg, D. E., *Organometallics* 2003, 22, 1968;
(21) Bahri-Laleh, N.; Credendino, R.; Cavallo, L., *Beilstein J. Org. Chem.* 2011, 7, 40.
(22) (a) Perdew, J. P.; Burke, K.; Ernzerhof, M., *Phys. Rev. Lett.* 1996, 77, 3865; (b) Perdew, J. P.; Burke, K.; Ernzerhof, M., *Phys. Rev. Lett.* 1997, 78, 1396.
(23) Frisch, M. J.; Trucks, G. W.; Schlegel, H. B.; Scuseria, G. E.; Robb, M. A.; Cheeseman, J. R.; J. A. Montgomery, J.; Vreven, T.; Kudin, K. N.; Burant, J. C.; Millam, J. M.; Iyengar, S. S.; Tomasi, J.; Barone, V.; Mennucci, B.; Cossi, M.; Scalmani, G.; Rega, N.; Petersson, G. A.; Nakatsuji, H.; Hada, M.; Ehara, M.; Toyota, K.; Fukuda, R.; Hasegawa, J.; Ishida, M.; Nakajima, T.; Honda, Y.; Kitao, O.; Nakai, H.; Klene, M.; Li, X.; Knox, J. E.; Hratchian, H. P.; Cross, J. B.; Adamo, C.; Jaramillo, J.; Gomperts, R.; Stratmann, R. E.; Yazyev, O.; Austin, A. J.; Cammi, R.; Pomelli, C.; Ochterski, J. W.; Ayala, P. Y.; Morokuma, K.; Voth, G. A.; Salvador, P.; Dannenberg, J. J.; Zakrzewski, V. G.; Dapprich, S.; Daniels, A. D.; Strain, M. C.; Farkas, O.; Malick, D. K.; Rabuck, A. D.; Raghavachari, K.; Foresman, J. B.; Ortiz, J. V.; Cui, Q.; Baboul, A. G.; Clifford, S.; Cioslowski, J.; Stefanov, B. B.; Liu, G.; Liashenko, A.; Piskorz, P.; Komaromi, I.; Martin, R. L.; Fox, D. J.; Keith, T.; Al-Laham, M. A.; Peng, C. Y.; Nanayakkara, A.; Challacombe, M.; Gill, P. M. W.; Johnson, B.; Chen, W.; Wong, M. W.; Gonzalez, C.; Pople, J. A. *Gaussian* 03, Revision B.04; Gaussian, Inc.: Pittsburgh Pa., 2003.
(24) (a) Dunning, T. H., *J. Chem. Phys.* 1970, 53, 2823; (b) Dunning Jr., T. H.; Hay, P. J., In *Methods of Electronic Structure Theory*, Schaefer III, H. F., Ed. Plenum Press: New York, 1977; pp 1.
(25) Bergner, A.; Dolg, M.; Kuechle, W.; Stoll, H.; Preuss, H., *Mol. Phys.* 1993, 80, 1431.
(26) (a) Andrae, D.; Haussermann, U.; Dolg, M.; Stoll, H.; Preuss, H., *Theor. Chim. Acta* 1990, 77, 123; (b) Martin, J. M. L.; Sundermann, A., *J. Chem. Phys.* 2001, 114, 3408.
(27) The Cambridge Structural Database (CSD) of Cambridge Crystallographic Data Centre (CCDC), version 5.32, updated November 2010,
(28) Halgren, T. A., *J. Comput. Chem.* 1996, 17, 490.
(29) Stewart, J. J. P., *J. Comput. Chem.* 1989, 10, 209,
(30) Spartan"08, Wavefunction, Inc.: Irvine, Calif., 2008.
(31) (a) Grimme, S., *J. Comput. Chem.,* 2006, 27, 1787; (b) Becke, A. D., *J. Chem. Phys.* 1997, 107, 8554; (c) Chai, J. D.; Head-Gordon, M., *Phys. Chem. Chem. Phys.* 2008, 10, 6615; (d) Wu, Q.; Yang, W. T., *J. Chem. Phys.* 2002, 116, 515.
(32) M. J. Frisch, G. W. T., H. B. Schlegel, G. E. Scuseria, M. A. Robb, J. R. C., G. Scalmani, V. Barone, B. Mennucci, G. A. Petersson, H. N., M. Caricato, X. Li, H. P. Hratchian, A. F. Izmaylov, J. B., G. Zheng, J. L. Sonnenberg, M. Hada, M. Ehara, K. T., R. Fukuda, J. Hasegawa, M. Ishida, T. Nakajima, Y. Honda, O. K., H. Nakai, T. Vreven, J. A. Montgomery, Jr., J. E. Peralta, F. O., M. Bearpark, J. J. Heyd, E. Brothers, K. N. Kudin, V. N. S., T. Keith, R. Kobayashi, J. Normand, K. Raghavachari, A. R., J. C. Burant, S. S. Iyengar, J. Tomasi, M. Cossi, N. R., J. M. Millam, M. Klene, J. E. Knox, J. B. Cross, V. Bakken, C. A., J. Jaramillo, R. Gomperts, R. E. Stratmann, O. Yazyev, A. J. A., R. Cammi, C. Pomelli, J. W. Ochterski, R. L. Martin, K. M., V. G. Zakrzewski, G. A. Voth, P. Salvador, J. J. D., S. Dapprich, A. D. Daniels, O. Farkas, J. B. F., J. V. Ortiz, J. Cioslowski, Fox, a. D. J. *Gaussian* 09, *Revision B*.01, Gaussian, Inc.: 2010.
(33) TZ (Dunning) T. H., *J. Chem. Phys.* 1971, 55, 716.
(34) Check, C. E.; Faust, T. O.; Bailey, J. M.; Wright, B. J.; Gilbert, T. M.; Sunderlin, L. S., *J. Phys. Chem. A* 2001, 105, 8111.
(35) Matsuda, H.; Watanabe, S.; Yamamoto, K., *Chem. Biodivers.* 2004, 1, 1985.
(36) (a) Connon, S. J.; Blechert, S., *Angew. Chem. Int. Ed.* 2003, 42, 1900; (b) Ding, X.; Lv, X. H.; Hui, B.; Chen, Z. J.; Xiao, M. L.; Guo, B. S.; Tang, W. N., *Tetrahedron Letters* 2006, 47, 2921.
(37) (a) Tomasi, J.; Persico, M., *Chem. Rev,* 1994, 94, 2027; (b) Cossi, M.; Scalmani, G.; Rega, N.; Barone, V., *J. Chem. Phys.* 2002, 117, 43.
(38) Brown, H. C.; Basavaiah, D.; Kulkarni, S. U.; Lee, H. D.; Negishi, E.; Katz, J. J., *J. Org. Chem.* 1986, 51, 5270.

The invention claimed is:

1. A compound of Formula (A), wherein:

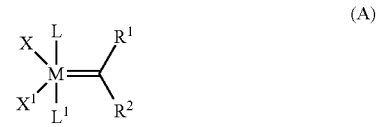

M is Ru;
$R^1$ is H;
$R^2$ and $L^1$ together are covalently linked to form a chelating multidentate ligand that is 2-alkyloxyphenyl;
$X^1$ is Y—W, wherein Y is S, and W is aryl optionally substituted with 1-20 electron-withdrawing groups selected from nitro, $CF_3$, halogen, CN, ester, keto, $C_{1-10}$ aliphatic group, or $C_{1-10}$ aromatic group;
X is halo; and
L is N-heterocyclic carbene ligand.

2. The compound of claim 1, wherein:
$R^2$ and $L^1$ together are covalently linked to form a chelating multidentate ligand that is 2-isopropoxyphenyl;
$X^1$ is Y—W, wherein Y is S; and
L is N,N'-bis (mesityl) imidazol-2-ylidene (IMes), N,N'-bis-(mesityl)-4,5-dihydroimidazol-2-ylidene ($H_2$IMes), N,N'-bis-[2,6-bis(1-methylethyl)phenyl]4,5-dihydro-imidazol-2-ylidene, N,N'-bis ($C_3$-$C_{12}$ aryl or $C_1$-$C_{12}$ alkyl) imidazol-2-ylidene, or N,N'-bis-($C_3$-$C_{12}$ aryl or $C_1$-$C_{12}$ alkyl)-4,5-dihydroimidazol-2-ylidene.

3. The compound of claim 1, wherein L is an imidazol-2-ylidene ligand.

4. The compound of claim 1, wherein W is 2,4,6-triphenyl-phenyl; 2,4,6-trimethyl-phenyl; 2,6-dimethyl-phenyl; or 2,6-dichloro-phenyl.

5. The compound of claim 1, wherein the most acute angle formed by M and Y—W is in the range of 90-120°.

6. A catalyst for catalysing olefin metathesis reactions comprising a compound of claim 1.

7. The catalyst of claim 6, wherein the olefin metathesis reaction comprises a reaction selected from ring-closing metathesis, ring-opening metathesis, cross-metathesis, and ring opening metathesis polymerization.

8. The catalyst of claim 6 which is capable of stereoselectively generating disubstituted olefinic products in a ring-closing metathesis reaction.

9. The catalyst of claim 6 which has a Z/E selectivity at least 10% (calculated on the total yield of Z and E products) higher than that obtained using an otherwise similar dichloro-substituted ruthenium catalyst.

10. The catalyst of claim 6 which is in free form or bound to a support.

* * * * *